US012611102B2

(12) United States Patent
Suzuki et al.

(10) Patent No.: US 12,611,102 B2
(45) Date of Patent: Apr. 28, 2026

(54) OPHTHALMIC APPARATUS

(71) Applicant: Topcon Corporation, Tokyo (JP)

(72) Inventors: Masaya Suzuki, Tokyo (JP); Kazuhiro Yamada, Tokyo (JP); Hitoshi Shimizu, Tokyo (JP); Masashi Nakajima, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 825 days.

(21) Appl. No.: 17/959,305

(22) Filed: Oct. 4, 2022

(65) Prior Publication Data

US 2023/0023425 A1 Jan. 26, 2023

Related U.S. Application Data

(63) Continuation of application No. PCT/JP2021/013984, filed on Mar. 31, 2021.

(30) Foreign Application Priority Data

Apr. 6, 2020 (JP) ................................. 2020-068050

(51) Int. Cl.
*A61B 3/12* (2006.01)
*A61B 3/14* (2006.01)
(52) U.S. Cl.
CPC ............ *A61B 3/1216* (2013.01); *A61B 3/145* (2013.01)
(58) Field of Classification Search
CPC ...................................................... A61B 3/145
(Continued)

(56) References Cited

U.S. PATENT DOCUMENTS 3,417,754 A * 12/1968 Smart .................. A61B 3/1208
606/18
4,422,736 A * 12/1983 Nunokawa ............. A61B 3/156
351/207
(Continued)

FOREIGN PATENT DOCUMENTS

CN 102281812 A 12/2011
CN 102755150 A 10/2012
(Continued)

OTHER PUBLICATIONS

Extended European Search Report issued Mar. 6, 2025, in corresponding EP Patent Application No. 24208600.7, 11pp.
(Continued)

*Primary Examiner* — Sharrief I Broome
(74) *Attorney, Agent, or Firm* — XSENSUS LLP

(57) ABSTRACT

An ophthalmic apparatus includes an illumination optical system and an imaging optical system. The illumination optical system includes a slit with a slit-shaped aperture and an iris aperture with two apertures and is configured to generate slit-shaped illumination light and to guide the illumination light to a fundus of a subject's eye. The imaging optical system includes an imaging aperture with an aperture, and is configured to guide returning light of the illumination light to an image sensor. A width of the slit-shaped aperture, a distance between the two apertures, and a size of the aperture in the imaging aperture are set so that an overlap region of a light flux region of the illumination light and a light flux region of the returning light is located on a side of the fundus from a posterior surface of lens of the subject's eye within the eye.

19 Claims, 16 Drawing Sheets

(58) Field of Classification Search
USPC ......................................................... 351/206
See application file for complete search history.

(56) References Cited

U.S. PATENT DOCUMENTS

| | | | |
|---|---|---|---|
| 5,471,261 A * | 11/1995 | Yoshizo ................. | A61B 3/145 |
| | | | 351/209 |
| 6,758,564 B2 * | 7/2004 | Ferguson ............. | A61B 3/1025 |
| | | | 351/221 |
| 7,831,106 B2 | 11/2010 | Elsner et al. | |
| 8,237,835 B1 | 8/2012 | Muller | |
| 2006/0177205 A1 * | 8/2006 | Steinkamp ............... | A61B 3/14 |
| | | | 396/18 |
| 2011/0273538 A1 | 11/2011 | Suzuki | |
| 2012/0069300 A1 * | 3/2012 | Kakuuchi ............... | A61B 3/14 |
| | | | 351/206 |
| 2012/0274904 A1 | 11/2012 | Saito et al. | |
| 2013/0128226 A1 | 5/2013 | Yahagi et al. | |
| 2015/0059239 A1 | 3/2015 | Andersson et al. | |
| 2015/0085252 A1 | 3/2015 | Fujimura et al. | |
| 2015/0272432 A1 * | 10/2015 | Satake ................. | A61B 3/0025 |
| | | | 351/246 |
| 2015/0272435 A1 * | 10/2015 | Ito ............................ | A61B 3/14 |
| | | | 351/206 |
| 2016/0100754 A1 * | 4/2016 | Dobashi ................... | A61B 3/12 |
| | | | 351/208 |
| 2016/0345822 A1 | 12/2016 | Fujimura et al. | |
| 2017/0303782 A1 | 10/2017 | Ito et al. | |
| 2020/0000335 A1 | 1/2020 | Yoshino | |
| 2022/0322935 A1 | 10/2022 | Suzuki et al. | |

FOREIGN PATENT DOCUMENTS

| | | | | | |
|---|---|---|---|---|---|
| CN | 103841820 | A | 6/2014 | | |
| CN | 104939802 | A | 9/2015 | | |
| EP | 3738501 | A1 * | 11/2020 | .......... | A61B 3/0025 |
| JP | 59-77829 | A | 5/1984 | | |
| JP | 61-293430 | A | 12/1986 | | |
| JP | H05199997 | A | 8/1993 | | |
| JP | 3243272 | B2 | 1/2002 | | |
| JP | 2010-259495 | A | 11/2010 | | |
| JP | 2012-34925 | A | 2/2012 | | |
| JP | 2013-248376 | A | 12/2013 | | |
| JP | 2016-30181 | A | 3/2016 | | |
| JP | 2016-140402 | A | 8/2016 | | |
| JP | 2020-6172 | A | 1/2020 | | |
| WO | 2012/020635 | A1 | 2/2012 | | |
| WO | 2021/149280 | A1 | 7/2021 | | |

OTHER PUBLICATIONS

Chinese Office Action issued Mar. 26, 2025, in corresponding CN Patent Application No. 202180025952.7, 14pp.
Extended European Search Report and Opinion received for European Patent Application No. 21783915.8, mailed on Apr. 10, 2024, 11 pages.
International Search Report and Written Opinion mailed on Jun. 22, 2021, received for PCT Application PCT/JP2021/013984, filed on Mar. 31, 2021, 8 pages including English Translation.
Escudero-Sanz et al., "Off-axis aberrations of a wide-angle schematic eye model", Journal of the Optical Society of America., vol. 16, No. 8, Aug. 1999, pp. 1881-1891.

* cited by examiner

FIG. 9

OPHTHALMIC APPARATUS

CROSS-REFERENCE TO RELATED APPLICATIONS

The present application is a continuation application of International Patent Application No. PCT/JP2021/013984, filed Mar. 31, 2021, which claims priority to Japanese Patent Application No. 2020-068050, filed Apr. 6, 2020, both of which are herein incorporated by reference in their entirety.

FIELD

The disclosure relates to an ophthalmic apparatus.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired.

For example, U.S. Pat. Nos. 7,831,106 and 8,237,835 disclose ophthalmic apparatuses configured to pattern-illuminate a subject's eye and to receive returning light thereof using an image sensor, using a rolling shutter method. These ophthalmic apparatuses can acquire images of the subject's eye with a simple configuration, by adjusting the illumination pattern and the timing of light receiving using the image sensor.

Further, for example, Japanese Unexamined Patent Publication No. 2016-30181 discloses a fundus imaging apparatus configured to also narrow reflected light from the fundus to a spot shape by entering the spot-shaped illumination light to the fundus, and to reduce the region where the light flux region of the illumination light and the light flux region of the reflected light intersect in the lens (crystalline lens).

SUMMARY

One aspect of some embodiments is an ophthalmic apparatus, including: an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the fundus from a posterior surface of lens of the subject's eye within the eye of the subject eye.

Another aspect of some embodiments is an ophthalmic apparatus, including: an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the subject's eye from an anterior surface of cornea of the subject's eye within the eye of the subject eye.

BRIEF EXPLANATION OF THE DRAWINGS

FIG. 9 is an explanatory diagram of an operation of the ophthalmic apparatus according to the embodiments.

3

Figure 13:
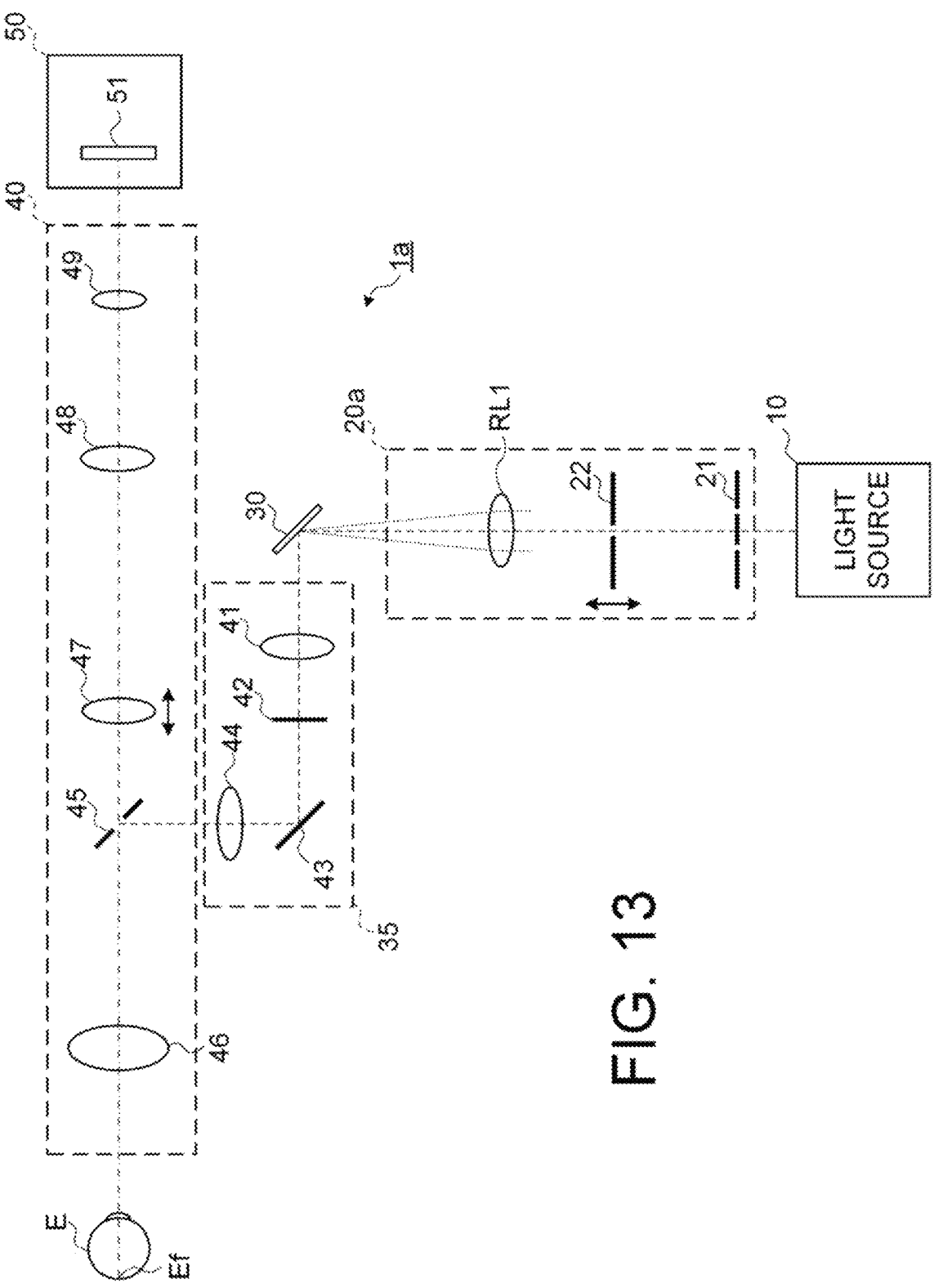

FIG. 13 is a schematic diagram illustrating an example of a configuration of an optical system of an ophthalmic apparatus according to a fifth modification example of the embodiments.

Figure 14:
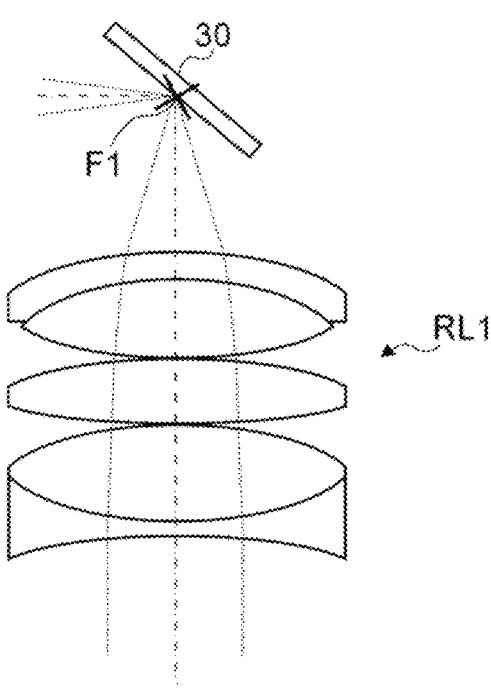

FIG. 14 is a schematic diagram illustrating an example of a configuration of an optical system of the ophthalmic apparatus according to the fifth modification example of the embodiments.

Figure 15:
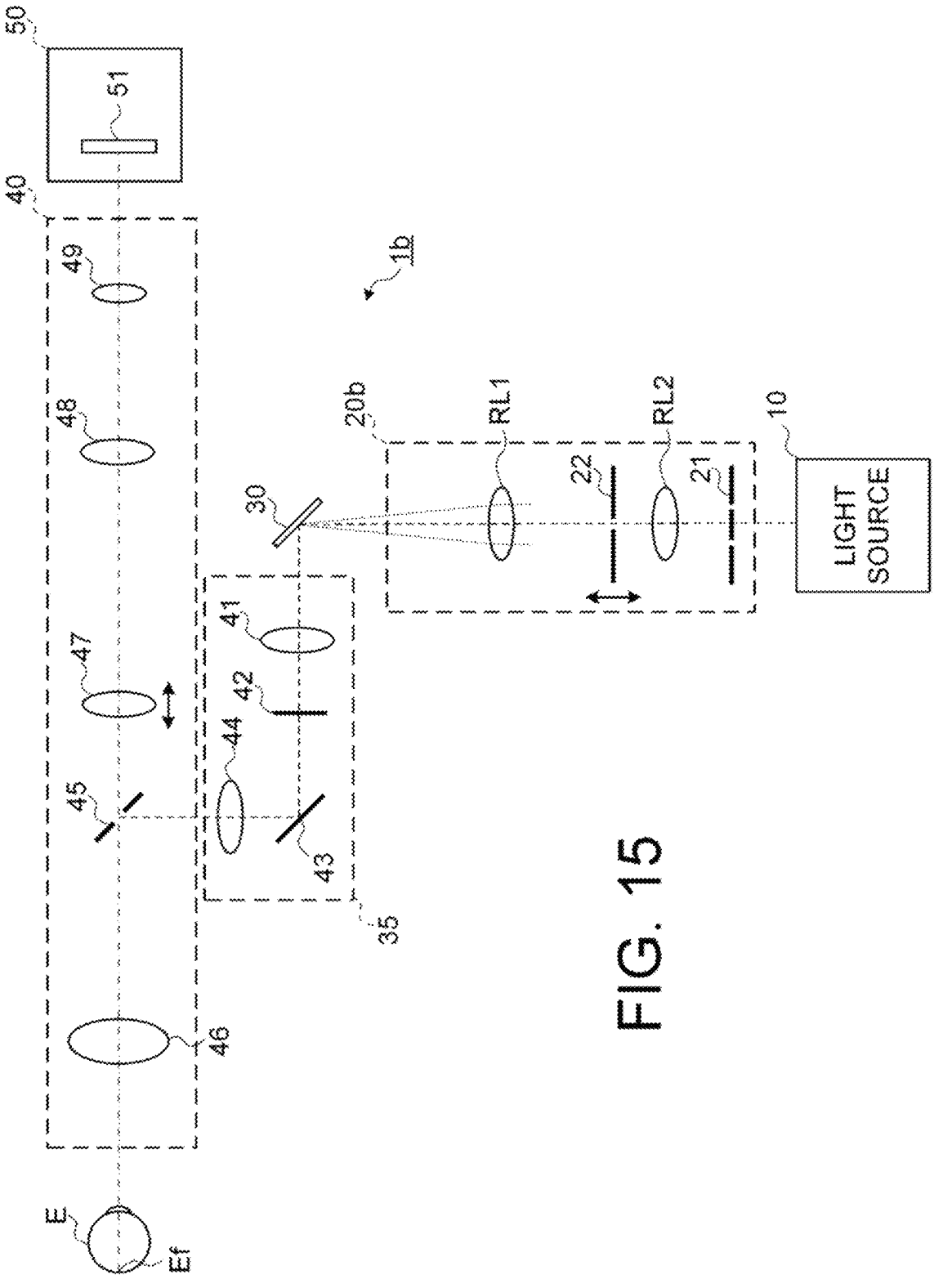

FIG. 15 is a schematic diagram illustrating an example of a configuration of an optical system of an ophthalmic apparatus according to a sixth modification example of the embodiments.

Figure 16:
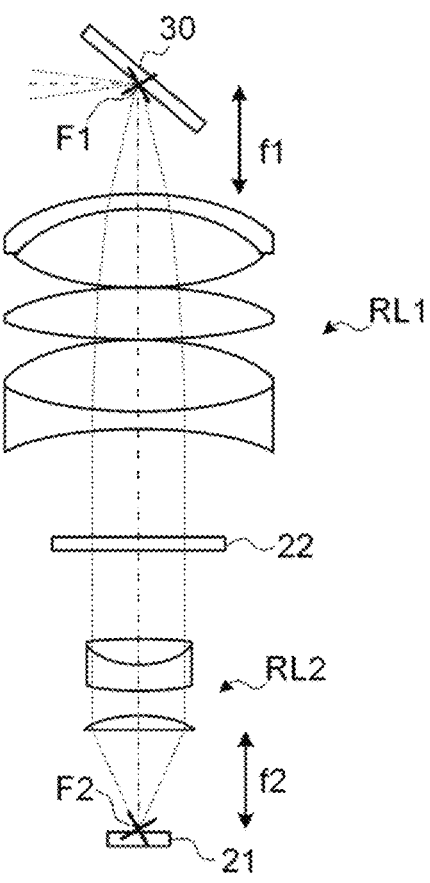

FIG. 16 is a schematic diagram illustrating an example of a configuration of an optical system of the ophthalmic apparatus according to the sixth modification example of the embodiments.

DETAILED DESCRIPTION

In the methods disclosed in U.S. Pat. Nos. 7,831,106 and 8,237,835, flare occurs due to the intersection of the light flux region of the illumination light and the light flux region of the reflected light in the lens, and even with a simple configuration, a problem is that the image quality of the acquired images of the subject's eye may be degraded.

In contrast, according to the method disclosed in Japanese Unexamined Patent Publication No. 2016-30181, the flare can be reduced. However, because it is necessary to irradiate the subject's eye with spot-shaped illumination light, it is necessary to modify the existing configuration and the timing adjustment between the illumination side and the light receiving side is complicated. In addition, the imaging time becomes longer. Thereby, the possibility of image quality degradation due to eye movement, etc. of the subject's eye increases.

According to some embodiments according to the present invention, a new technique for acquiring a high quality image of a subject's eye with a simple configuration can be provided.

Referring now to the drawings, exemplary embodiments of an ophthalmic apparatus according to the present invention are described below. The contents of the document cited in the present specification can be appropriately incorporated as contents of the following embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmic apparatus according to embodiments illuminates a predetermined site of a subject's eye while moving an irradiated position (illumination region, irradiated range) of slit-shaped illumination light, and receives returning light from the predetermined site using an image sensor with a one-dimensional or two-dimensional array of light receiving elements. Light receiving result of the returning light is read out from the light receiving elements at light receiving position of the returning light corresponding to the irradiated position of the illumination light, in synchronization with the movement timing of the irradiated position of the illumination light. In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, a case where the ophthalmic apparatus according to the embodiments acquires images of the fundus of the subject's eye mainly will be described.

[Configuration of Optical System]

Figure 1:
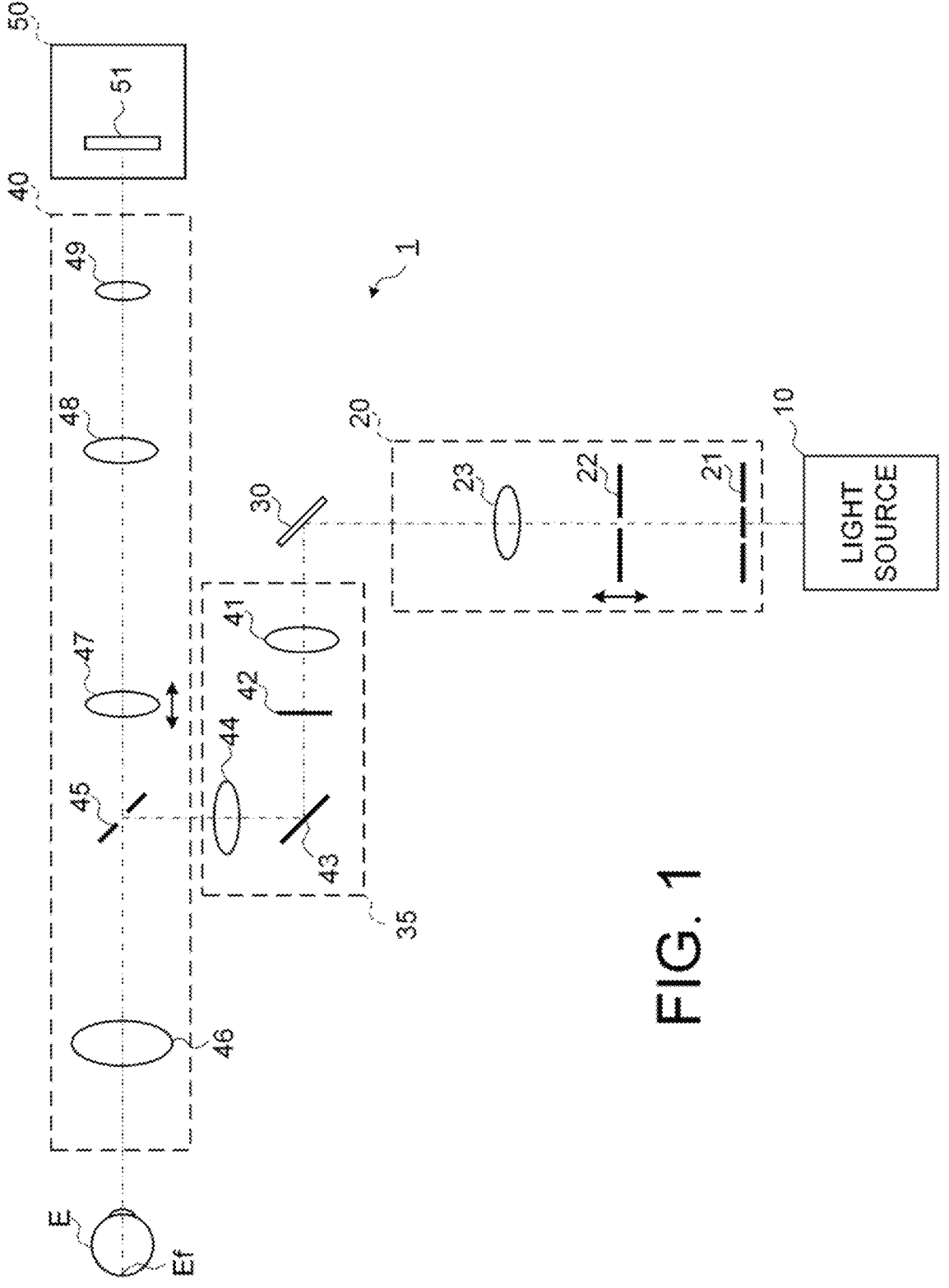
FIG. 1 is a schematic diagram illustrating an example of a configuration of an optical system of an ophthalmic apparatus according to embodiments.
Figure 2:
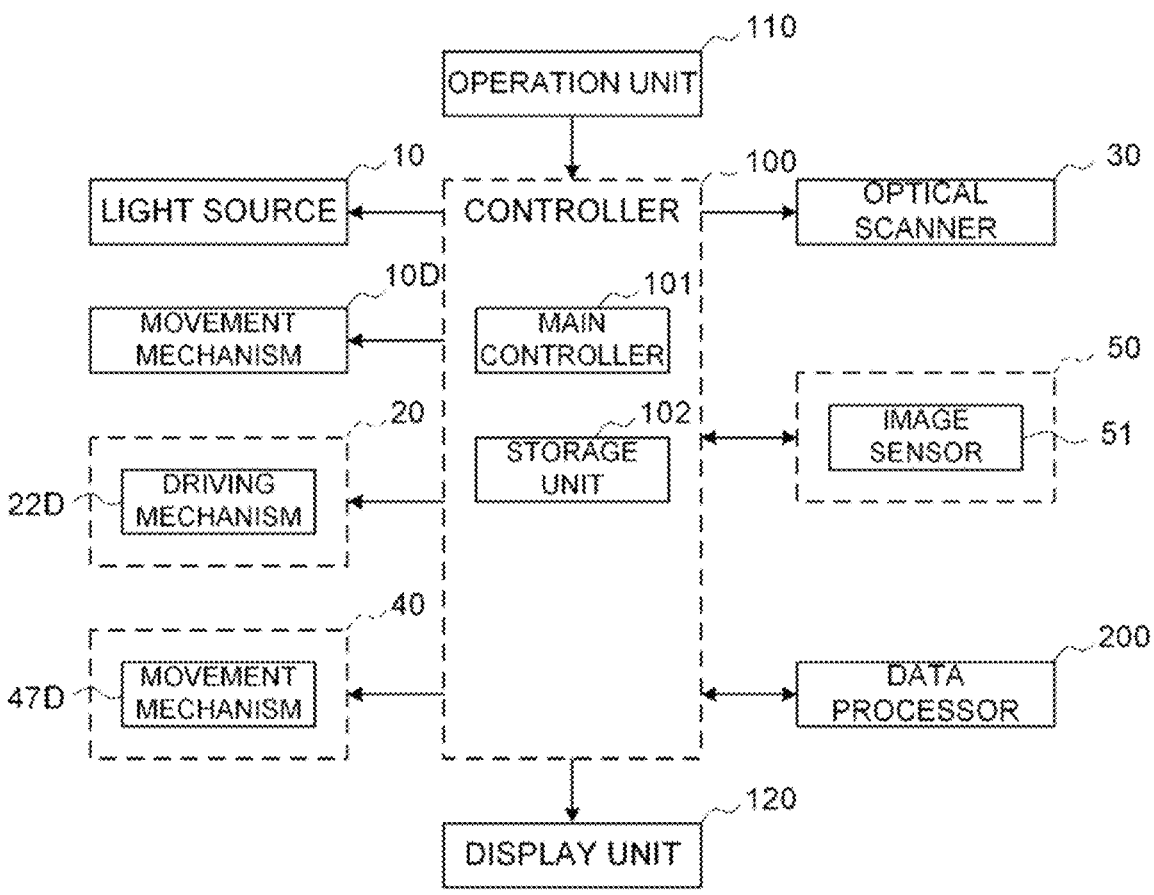
FIG. 2 is a schematic diagram illustrating an example of a configuration of a control system of the ophthalmic apparatus according to the embodiments.
Figure 3A:
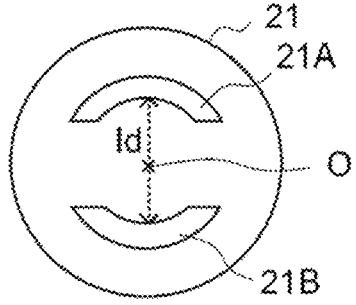
FIG. 3A is a schematic diagram illustrating an example of a configuration of an optical system of the ophthalmic apparatus according to the embodiments.
Figure 3B:
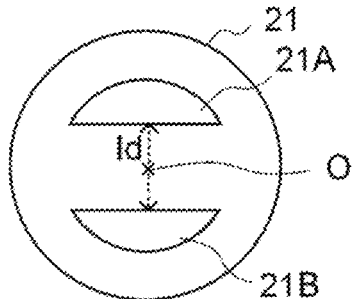
FIG. 3B is a schematic diagram illustrating an example of a configuration of an optical system of the ophthalmic apparatus according to the embodiments.

FIG. 1, FIG. 2, FIG. 3A, and FIG. 3B show schematic diagrams of an example of a configuration of an ophthalmic apparatus according to embodiments. FIG. 1 represents an example of a configuration of an optical system of the ophthalmic apparatus 1 according to the embodiments. FIG. 2 representing a block diagram of an example of a configuration of a control system (processing system) of the ophthalmic apparatus 1 according to the embodiments. FIG. 3A schematically represents an example of the first configuration of an iris aperture 21 in FIG. 1 when viewed from a direction of an optical axis O. FIG. 3B schematically represents an example of the second configuration of an iris aperture 21 in FIG. 1 when viewed from a direction of an optical axis O. In FIGS. 1 to 3B, like parts are designated by like reference numerals as in repetitious description of such parts may not be provided.

The ophthalmic apparatus 1 includes a light source 10, an illumination optical system 20, an optical scanner 30, a projection optical system 35, and an imaging optical system 40, and an imaging device 50. In some embodiments, the illumination optical system 20 includes at least one of the light source 10, the optical scanner 30, and the projection optical system 35. In some embodiments, the imaging optical system 40 includes the imaging device 50. In some embodiments, the projection optical system 35 or the imaging optical system 40 includes the optical scanner 30.

(Light Source 10)

The light source 10 includes a visible light source that generates light in the visible region. For example, the light source 10 generates light having a central wavelength in the wavelength range of 420 nm to 700 nm. This type of light source 10 includes, for example, an LED (Light Emitting Diode), an LD (Laser Diode), a halogen lamp, or a xenon lamp. In some embodiments, the light source 10 includes a white light source or a light source capable of outputting light with each color component of RGB. In some embodiments, the light source 10 includes a light source capable of switching to output the light in infrared region or the light in visible region. The light source 10 is arranged at a position non-conjugate optically to each of a fundus Ef and the iris.

(Illumination Optical System 20)

The illumination optical system 20 generates slit-shaped illumination light using the light from the light source 10. The illumination optical system 20 guides the generated illumination light to the optical scanner 30.

The illumination optical system 20 includes the iris aperture 21, the slit 22, and a relay lens 23. The light from the light source 10 passes through the aperture(s) formed in the iris aperture 21, passes through the aperture formed in the slit 22, and is transmitted through the relay lens 23. The relay lens 23 includes one or more lenses. The light transmitted through the relay lens 23 is guided to the optical scanner 30.

(Iris Aperture 21)

The iris aperture 21 (specifically, aperture(s) described below) can be arranged at a position substantially conjugate optically to the iris (pupil) of a subject's eye E. In the iris aperture 21, one or more apertures are formed at position(s) away from the optical axis O.

For example, as shown in FIG. 3A, apertures 21A and 21B having a predetermined thickness along a circumferential direction centered with the optical axis O are formed in the iris aperture 21. A distance Id between the aperture 21A and the aperture 21B is a distance in a direction passing through the optical axis position.

For example, as shown in FIG. 3B, apertures 21A and 21B having a circular segment shaped (bow-shaped) along a circumferential direction centered with the optical axis O are formed in the iris aperture 21. A distance Id between the aperture 21A and the aperture 21B is a distance in a direction passing through the optical axis position.

The aperture(s) formed in the iris aperture 21 defines an incident position (incident shape) of the illumination light on the iris of the subject's eye E. For example, when the pupil center of the subject's eye E is arranged on the optical axis O, the illumination light can enter into the eye from positions deviated from the pupil center (specifically, point-symmetrical positions centered on the pupil center), by forming the apertures 21A and 21B as shown in FIG. 3A or FIG. 3B.

The shape of the aperture(s) formed in the iris aperture 21 is not limited to the arc shape in FIG. 3A or the bow shape shown in FIG. 3B. In some embodiment, the apertures 21A and 21B are rectangular in shape, respectively. In some embodiment, the apertures 21A and 21B are elliptical shape, respectively.

Further, the light amount distribution of the light passing through the aperture(s) formed in the iris aperture 21 can be changed by changing a relative position between the light source 10 and the aperture(s) formed in the iris aperture 21.

(Slit 22)

The slit 22 (specifically, aperture(s) described below) can be arranged at a position substantially conjugate optically to the fundus Ef of the subject's eye E. For example, in the slit 22, the aperture is formed extending in a direction corresponding to a line direction (row direction) that is read out from the image sensor 51 described below using the rolling shutter method. The aperture formed in the slit 22 defines an irradiated pattern of the illumination light on the fundus Ef of the subject's eye E.

The slit 22 can be moved in the optical axis direction of the illumination optical system 20 using a driving mechanism (driving mechanism 22D described below). The driving mechanism moves the slit 22 in the optical axis direction, under the control from the controller 100 described below. For example, the controller 100 controls the driving mechanism in accordance with the state of the subject's eye E. This allows to move the position of the slit 22 in accordance with the state of the subject's eye E (specifically, the dioptric power or the shape of the fundus Ef).

In some embodiments, the slit 22 is configured so that at least one of the position of the aperture and the shape of the aperture can be changed in accordance with the state of the subject's eye E without being moved in the optical axis direction. The function of the slit 22 with this configuration is, for example, realized by a liquid crystal shutter.

The light from the light source 10 that has passed through the aperture(s) formed in the iris aperture 21 is output as the slit-shaped illumination light by passing through the aperture formed in the slit 22. The slit-shaped illumination light is transmitted through the relay lens 23, and is guided to the optical scanner 30.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture formed in the slit 22). Specifically, the optical scanner 30 deflects the slit-shaped illumination light for sequentially illuminating a predetermined irradiated region of the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illumination light one-dimensionally or two-dimensionally.

In case that the optical scanner 30 deflects the illumination light one-dimensionally, the optical scanner 30 includes a galvano scanner that deflects the illumination light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the illumination optical system 20. The second galvano scanner deflects light deflected by the first galvano scanner so as to move the irradiated position of the illumination light in a vertical direction orthogonal to the optical axis of the illumination optical system 20. Examples of scan mode for moving the irradiated position of the illumination light using the optical scanner 30 include a horizontal scan, a vertical scan, a cross scan, a radial scan, a circle scan, a concentric scan, and a helical (spiral) scan.

(Projection Optical System 35)

The projection optical system 35 guides the illumination light deflected by the optical scanner 30 to the fundus Ef of the subject's eye E. In the embodiments, the projection optical system 35 guides the illumination light deflected by the optical scanner 30 through an optical path coupled with an optical path of the imaging optical system 40 by a perforated mirror 45 as the optical path coupling member described below.

The projection optical system 35 includes a relay lens 41, a black point plate 42, a reflective mirror 43, and a relay lens 44. Each of the relay lenses 41 and 44 includes one or more lenses.

(Black Point Plate 42)

The black point plate 42 is arranged at a position substantially conjugate optically to a lens surface of an objective lens 46 or the vicinity of the lens surface of the objective lens 46. This prevents the reflected light from the lens surface of the objective lens 46 from being guided to the imaging device 50.

With such projection optical system 35, the illumination light deflected by the optical scanner 30 is transmitted through the relay lens 41, passes through the black point plate 42, is reflected by the reflective mirror 43 toward the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, a focusing lens 47, a relay lens 48, and an imaging lens 49. Each of relay lens 48 includes one or more lenses.

(Perforated Mirror 45)

In the perforated mirror 45, the hole is formed. The hole is arranged on the optical axis of the imaging optical system 40. The hole of the perforated mirror 45 is arranged at a position substantially conjugate optically to the iris of the subject's eye E. The perforated mirror 45 reflects the illumination light from the projection optical system 35 toward the objective lens 46, on the peripheral region of the hole. The perforated mirror 45 with this configuration functions as an imaging aperture (photographic stop (diaphragm)).

That is, the perforated mirror 45 is configured to couple the optical path of the illumination optical system 20 (projection optical system 35) and the optical path of the imaging optical system 40 arranged in a direction of the optical axis passing through the hole, and also to guide the illumination light reflected on the peripheral region of the hole to the fundus Ef.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light from the projection optical system 35 is reflected toward the objective lens 46 on the peripheral region of the hole formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, and is imaged on the light receiving surface of the image sensor 51 in the imaging device 50 through the imaging lens 49.

(Imaging Device 50)

The imaging device 50 includes the image sensor 51 receiving the returning light of the illumination light that has been guided from the fundus Ef of the subject's eye E through the imaging optical system 40. The imaging device 50 can output the light receiving result of the returning light under the control from the controller 100 described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result acquired by the image sensor 51 is read out using a rolling shutter method. In some embodiments, the controller 100 described below performs readout control of the light receiving result by controlling the image sensor 51. In some embodiments, the image sensor 51 can automatically output the light receiving results for a predetermined number of lines, along with information indicating the light receiving position(s).

The image sensor 51 with this configuration includes the CMOS image sensor. In this case, the image sensor 51 includes a plurality of pixels (light receiving elements). The plurality of pixels includes a plurality of pixel groups arranged in a column direction. Each of the plurality of pixel groups includes pixels arranged in a row direction. Specifically, the image sensor 51 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual opening shape extending in the row direction is acquired. Such control is disclosed in, for example, U.S. Pat. No. 8,237,835.

Figure 4:
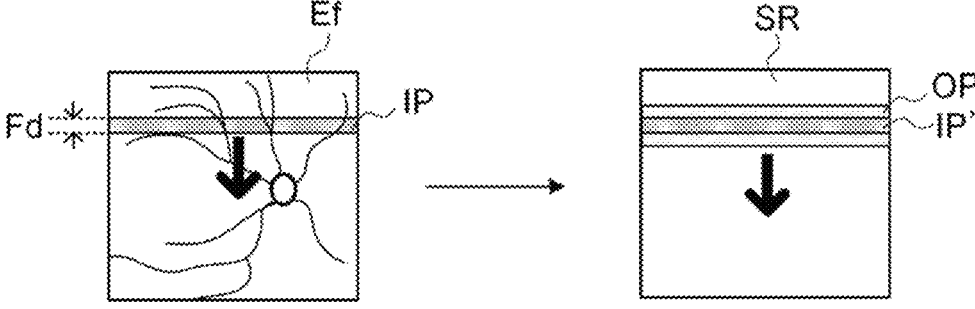
FIG. 4 is an explanatory diagram of an operation of the ophthalmic apparatus according to the embodiments.

FIG. 4 shows a diagram explaining the operation of the ophthalmic apparatus 1 according to the embodiments. FIG. 4 schematically represents an irradiated range IP of the slit-shaped illumination light irradiated on the fundus Ef and a virtual opening range OP on the light receiving surface SR of the image sensor 51.

For example, the controller 100 described below deflects the slit-shaped illumination light formed by the illumination optical system 20, using the optical scanner 30. Thereby, the irradiated range IP of the slit-shaped illumination light is sequentially moved (shifted) in a direction (for example, the vertical direction) orthogonal to the slit direction (for example, the row direction, the horizontal direction) on the fundus Ef.

On the light receiving surface SR of the image sensor 51, for example, by changing the pixels to be captured in units of lines by the controller 100 described below, the virtual opening range (opening region) OP is set. The opening range OP is preferable to be the light receiving range IP' of the returning light of the illumination light on the light receiving surface SR or wider than the light receiving range IP'. For example, the controller 100 described below performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

Figure 5:
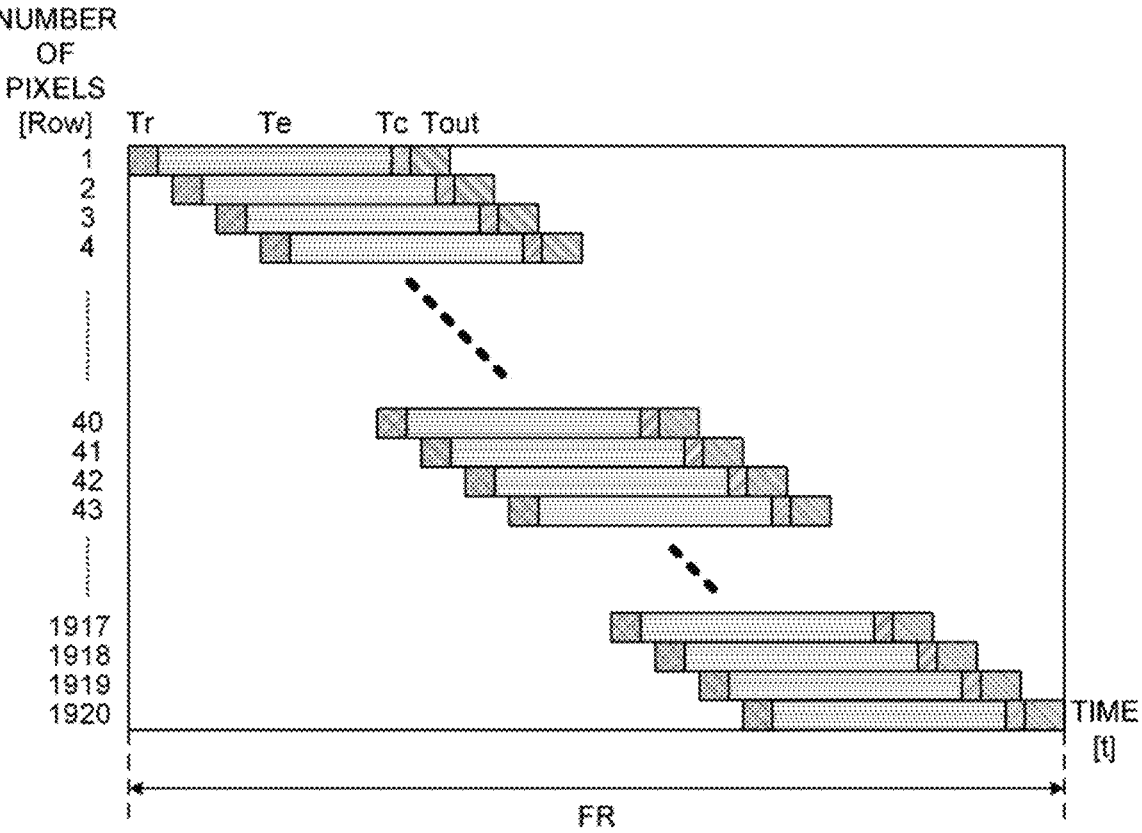
FIG. 5 is an explanatory diagram of an operation of the ophthalmic apparatus according to the embodiments.
Figure 6:
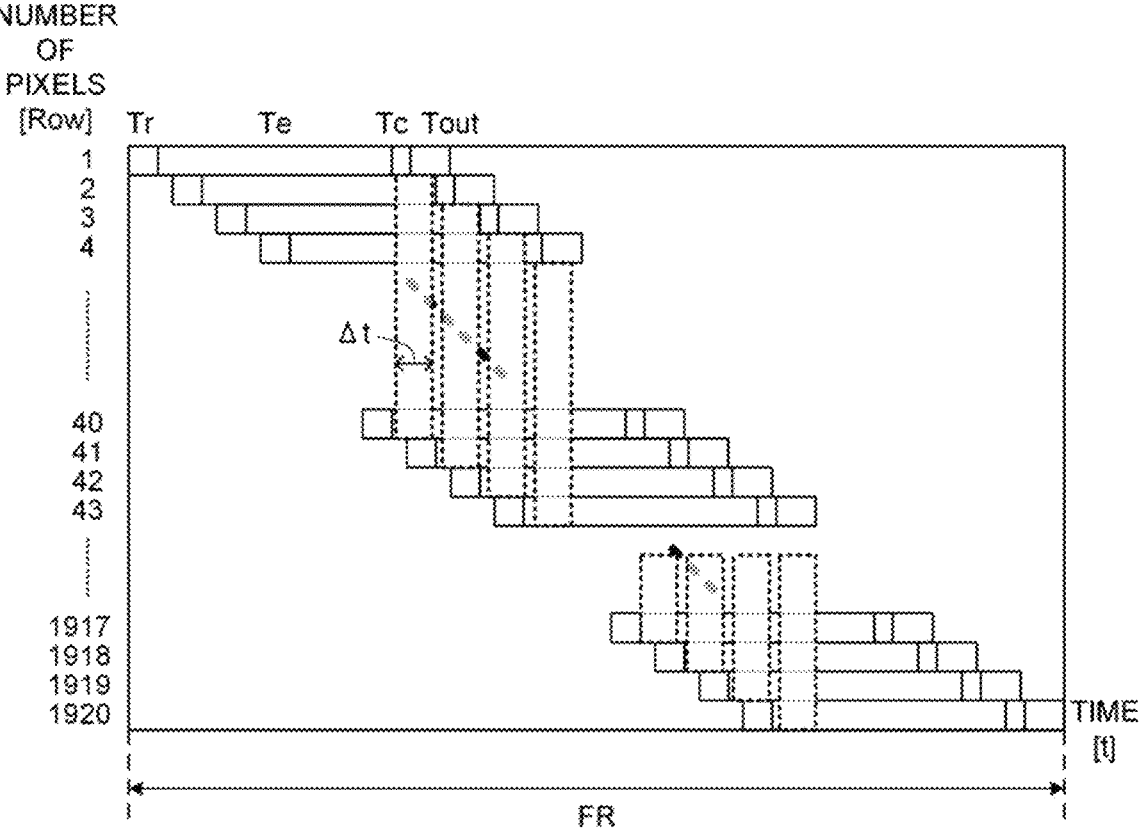
FIG. 6 is an explanatory diagram of an operation of the ophthalmic apparatus according to the embodiments.

FIGS. 5 and 6 schematically show examples of the control timing of the rolling shutter method for the image sensor 51. FIG. 5 represents an example of the timing of the readout control for the image sensor 51. FIG. 6 represents the timing of the movement control for the irradiated range IP (the light receiving range IP') superimposed on the timing of the readout control in FIG. 5. In FIGS. 5 and 6, the horizontal axis represents the number of rows in the image sensor 51, and the vertical axis represents time.

In addition, in FIGS. 5 and 6, for convenience of explanation, it is assumed that the number of rows in the image sensor 51 is 1920. However, the configuration according to the embodiments is not limited to the number of rows. Further, in FIG. 6, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 5, the readout time T for reading out the electrical charge accumulated in the pixels in the row direction is the sum of the time Tr required for the reset control, the time Te required for the exposure control (exposure time), the time Tc required for the charge transfer control, and the time Tout required for the output control.

In FIG. 5, by shifting the readout (capturing) start timing (start timing of time Tc) in units of rows, the light receiving results (amount of electrical charge) accumulated in the pixels in the desired range in the image sensor 51 are acquired. For example, in case that the pixel range shown in FIG. 5 is for a single frame of the image, the frame rate FR is determined uniquely.

In this embodiment, the irradiated position of the illumination light on the fundus Ef, the illumination light having a slit width of a plurality of rows, is sequentially shifted in a direction corresponding to the column direction on the fundus Ef. When the width in the shift direction of the irradiated range IP' (a region corresponding to the illumination region on the fundus Ef) on the light receiving surface of the image sensor 51 has two or more rows, the controller 100 described below controls the optical scanner 30 so that the opening range OP (opening region) shifts in the shift direction in units of a predetermined number of rows.

For example, as shown in FIG. 6, at each predetermined shift time Δt, the irradiated position of the illumination light on the fundus Ef is shifted in row units in the direction corresponding to the column direction. The shift time Δt is obtained by dividing the exposure time Te of the pixel in the image sensor 51 by the slit width (e.g., the number of rows of the slit width=40) of the illumination light (Δt=Te/40). Synchronized with this movement timing of this irradiated position, the readout start timing of each row of pixels is delayed and is started for each row in units of shift time Δt. This allows to acquired high quality images of the fundus Ef with strong contrast in a short time with a simple control.

In some embodiments, the image sensor 51 is configured using one or more line sensors.

[Configuration of Control System]

As shown in FIG. 2, the control system of the ophthalmic apparatus 1 is configured with a controller 100 as a center. It should be noted that at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the light source 10, control for a movement mechanism 10D, control for the illumination optical system 20, control for the optical scanner 30, control for the imaging optical system 40, control for the imaging device 50, and control for the data processor 200.

The control for the light source 10 includes switching the light source on and off (or switching the wavelength region of the light), and changing the light amount of the light source.

The movement mechanism 10D changes at least one of the position of the light source 10 and the orientation of the light source 10 using a known mechanism. The main controller 101 can change at least one of a relative position of the light source 10 to the iris aperture 21 and the slit 22, and a relative orientation of the light source 10 to the iris aperture 21 and the slit 22.

The control for the illumination optical system 20 includes control for the driving mechanism 22D. The driving mechanism 22D moves the slit 22 in the optical axis direction of the illumination optical system 20. The main controller 101 controls the driving mechanism 22D in accordance with the state of the subject's eye E to arrange the slit 22 at the position corresponding to the state of the subject's eye E. Examples of the state of the subject's eye E includes a shape of the fundus Ef, a dioptric power, and an axial length. The dioptric power can be obtained from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the dioptric powers in advance. The main controller 101 specifies the position of the slit 22 corresponding to the dioptric power by referring to the first control information, and controls the driving mechanism 22D so as to arrange the slit 22 at the specified position.

Here, as the slit 22 moves, the light amount distribution of the light passing through the aperture formed in the slit 22 changes. In this case, as described above, the main controller 101 can control the movement mechanism 10D to change at least one of the position of the light source 10 or the orientation of the light source 10.

The control for the optical scanner 30 includes control of the angle of the deflection surface deflecting the illumination light. By controlling an angle range of the deflection surface, the scan range (scan start position and scan end position) can be controlled. By controlling a change speed of the angle of the deflection surface, the scan speed can be controlled.

The control for the imaging optical system 40 includes a control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 51. Further, the main controller 101 can control the movement mechanism 47D based on a content of operation of the user using an operation unit 110 described below.

The control for the imaging device 50 includes a control for the image sensor 51. The control for the image sensor 51 includes a control for reading out the light receiving result using a rolling shutter method (for example, setting of light receiving size corresponding to the size of the illumination pattern, or the like). Further, the control for the image sensor 51 includes the reset control, the exposure control, the charge transfer control, and the output control. The time Tr required for the reset control, the time (exposure time) Te required for the exposure control, the time Tc required for the charge transfer control, and the time Tout required for the output control, etc., can be changed.

Example of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results. Examples of the analysis processing include a specifying processing of the in-focus state.

The data processor 200 can form the light receiving image corresponding to the arbitrary opening range based on the light receiving result(s) read out from the image sensor 51 using the rolling shutter method. The data processor 200 can sequentially form light receiving light images corresponding to the opening ranges and can form an image of the subject's eye E from a plurality of formed light receiving images, as an image forming unit.

The data processor 200 includes a processor, and realizes the above functions by performing processing corresponding to the program(s) stored in the storage unit or the like.

In some embodiments, the light source 10 includes two or more light sources. In this case, each of the two or more light sources is provided corresponding to the two or more apertures formed in the iris aperture 21. The main controller 101 can change the at least one of a position of each light source and an orientation (orientation in the direction of maximum light amount distribution) of each light source, by controlling the movement mechanisms provided for each of the two or more light sources.

(Storage Unit 102)

The storage unit 102 stores various computer programs and data. The computer programs include an arithmetic program and a control program for controlling the ophthalmic apparatus 1.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content for the operation unit 110 is fed to the controller 100 as electrical signals. Moreover, operations and inputs of information may be performed using a graphical user interface (GUI) displayed on the display unit 120 and the operation unit 110. In some embodiments, the functions of the display unit 120 and the operation unit 110 are realized a touch screen.

(Other Configurations)

In some embodiments, the ophthalmic apparatus 1 further includes a fixation projection system. For example, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor 200 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 200 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor 200 analyzes data processor segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

As described above, in the ophthalmic apparatus 1, the slit 22 (aperture), an imaging site (fundus Ef), and the image sensor 51 (light receiving surface) are arranged at positions substantially conjugate optically each other. The ophthalmic apparatus 1 can acquire a clear image of the imaging site while suppressing the effects due to the unnecessary scattered light, by moving the light receiving opening on the image sensor 51 in conjunction with the irradiated position of the illumination light.

In the embodiments, a width Fd of an image of the slit (width of an image of the aperture) formed in slit 22 on the fundus Ef, a distance Id between the images of the apertures 21A and 21B formed in the iris aperture 21 on the iris, and a size (radius, diameter) Sd of an image of the hole formed in the perforated mirror 45 (aperture formed in the imaging aperture) on the iris are set so that an overlap region of a light flux region of the illumination light and a light flux region of the returning light is located on a side of the fundus Ef from a posterior surface of lens of the subject's eye E within the eye of the subject eye E. This allows to reduce the occurrence of the flare on the posterior surface of the lens caused by the intersection of the light flux region of the illumination light and the light flux region of the returning light within the crystalline lens (lens).

In some embodiments, the width Fd of the image of the slit described above, the distance Id between the images of the two apertures described above, and the size Sd of the image of the hole are set so that the overlap region described above is located on the side of the subject's eye E from an anterior surface of cornea of the subject's eye E within the eye of the subject's eye E. This allows to reduce the occurrence of the flare on the anterior surface of cornea caused by the intersection of the light flux region of the illumination light and the light flux region of the returning light between the anterior surface of cornea and the crystalline lens (lens).

In some embodiments, the slit width Fd described above, the distance Id described above, and the size Sd of the hole described above are set so as to reduce the occurrence of the flare on any one of the posterior surface of lens and the anterior surface of cornea.

In the following embodiments, a case where the slit width Fd described above, the distance Id described above, and the size Sd of the hole described above are set so as to suppress the occurrence of the flare on the posterior surface of the lens and the anterior surface of the cornea, respectively will be described specifically.

First, a coordinate system is defined for defining the light flux region of the illumination light and the light flux region of the returning light. Hereinafter, the returning light of the illumination light may be referred to as the imaging light.

It should be noted that in the following, the distance between each site is assumed to be a path length (air conversion distance) without considering the refraction of the lens of the eye. In other words, since the illumination light and the imaging light (returning light) enter the eye at roughly the same incident angle and at roughly the same height, the illumination light and the imaging light are assumed to be affected by the same refraction effect. When the refraction effect is the same, there is no effect on the relative relationship between the light flux region of the illumination light and the light flux region of the imaging light (the position(s) of intersection point(s) the illumination light ray and the imaging light ray) and the site within the eye such as the cornea, the crystalline lens, and the fundus.

Figure 7:
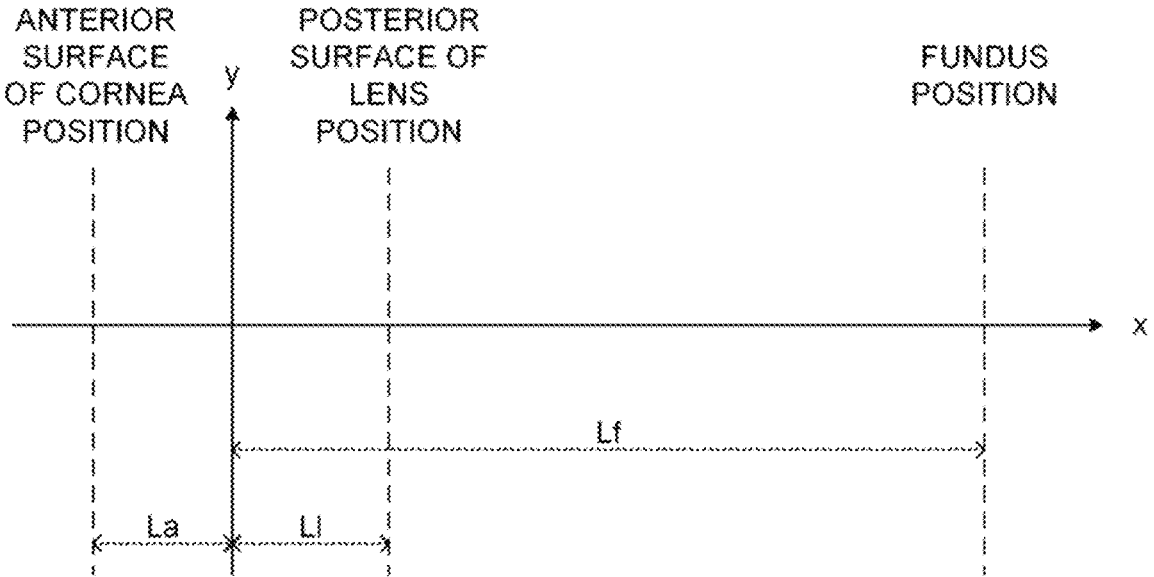
FIG. 7 is an explanatory diagram of the operation of the ophthalmic apparatus according to the embodiments.

FIG. 7 shows an example of the coordinate system for defining the light flux region(s) passing within the eye according to the embodiments. In FIG. 7, the horizontal axis represents the x-axis indicating the position of the site in the eye in the optical axis direction of the imaging optical system 40 (illumination optical system 20), and the vertical axis represents the y-axis indicating the position in the eye in the direction perpendicular to the optical axis of the imaging optical system 40 (illumination optical system 20). It should be noted that the origin position of the coordinate system in FIG. 7 is the pupil center position corresponding to the pupil center of the subject's eye E.

In the coordinate system shown in FIG. 7, the distance in the x direction between the anterior surface of cornea position corresponding to the anterior surface of cornea and the pupil center position (origin position) corresponding to the pupil center represents as La (La>0), the distance in the x direction between the pupil center position and the posterior surface of lens position corresponding to the posterior surface of lens represents as LI (LI>0), and the distance in the x direction between the pupil center position and the fundus position represents as LF (Lf>0).

<Suppression of the Occurrence of the Flare on the Posterior Surface of the Lens>

Next, in the coordinate system defined as shown in FIG. 7, the x-coordinate position of the position of an intersection point of the illumination light ray and the imaging light ray is obtained in order to specify the limit(s) of the overlap region between the light flux region of the illumination region and the light flux region of the imaging light that causes the flare on the posterior surface of lens.

Figure 8:
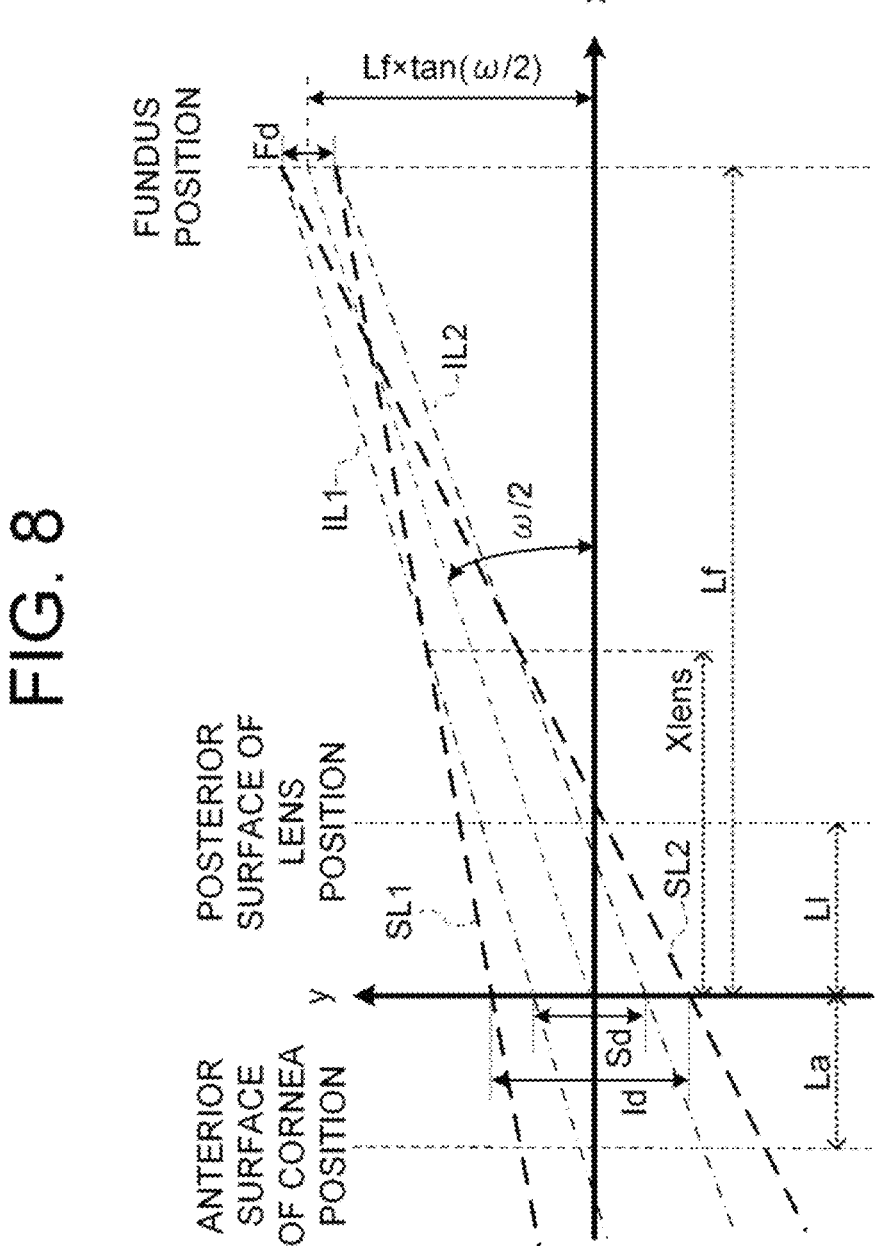
FIG. 8 is an explanatory diagram of an operation of the ophthalmic apparatus according to the embodiments.

FIG. 8 shows a diagram explaining the overlap region between the light flux region of the illumination light and the light flux region of the imaging light that causes the flare on the posterior surface of lens. FIG. 8 schematically represents the light ray of the illumination light and the light ray of the imaging light in a state where the alignment is completed (the optical axis of the imaging optical system 40 is aligned with the corneal apex). In FIG. 8, parts similar to those in FIG. 7 are denoted by the same reference symbols, and description thereof is omitted as appropriate. In FIG. 8 the imaging angle of view is represented as ω.

As described above, the apertures 21A and 21B in the iris aperture 21 and the hole formed in the perforated mirror 45 are arranged at positions substantially conjugate optically to the iris (that is, pupil center) of the subject's eye E. Therefore, in FIG. 8, the distance Id between the apertures 21A and 21B in the iris aperture 21, and the size (radius) Sd of the hole formed in the perforated mirror 45 are defined at the pupil center position.

Further, as described above, the slit 22 is arranged at a position substantially conjugate optically to the fundus Ef of the subject's eye E. Therefore, in FIG. 8, the slit width Fd of the slit 22 is defined at the fundus position.

In this case, the illumination light passes through the apertures 21A and 21B in the iris aperture 21, passes through the aperture formed in the slit 22, and reaches the fundus Ef.

This light flux region of the illumination region is demarcated by the illumination light rays SL1 and SL2 shown in FIG. 8. Specifically, in FIG. 8, the light flux region of the illumination light passing through the aperture 21A of the iris aperture 21 is an upper region in the y direction from the illumination light ray SL1, and the light flux region of the illumination light passing through aperture 21B of the iris aperture 21 is a lower region in the y direction from the illumination light ray SL2.

As shown in FIG. 8, the illumination light ray SL1 is represented by a straight line connecting a lower edge of the aperture 21A of the iris aperture 21 (the upper edge of the light shielding region including the optical axis position in the iris aperture 21) at the pupil center position and a lower edge of the aperture in the slit 22 at the fundus position. The coordinate position of the lower edge of the aperture 21A is (0, Id/2). The coordinate position of the lower edge of the aperture in the slit 22 is (Lf, Lf×tan(ω)/2)−Fd/2). Therefore, the illumination light ray SL1 is represented as in Equation (1).

[Equation 1]

$$y = \frac{Lf \times \tan\left(\frac{\omega}{2}\right) - \frac{Fd}{2} - \frac{Id}{2}}{Lf} \times x + \frac{Id}{2} \quad (1)$$

As shown in FIG. 8, the illumination light ray SL2 is represented by a straight line connecting an upper edge of the aperture 21B of the iris aperture 21 (the lower edge of the light shielding region including the optical axis position in the iris aperture 21) at the pupil center position and an upper edge of the aperture in the slit 22 at the fundus position. The coordinate position of the lower edge of the aperture 21A is (0, −Id/2). The coordinate position of the lower edge of the aperture in the slit 22 is (Lf, Lf×tan(ω/2)+Fd/2). Therefore, illumination light ray SL2 can be derived in the same way as the illumination light ray SL1.

On the other hand, the returning light of the illumination light from the fundus Ef (imaging light) passes through the hole formed in the perforated mirror 45 from the irradiated position of the illumination light on the fundus Ef, and is guided to the image sensor 51.

This light flux region of the returning light of the illumination region is demarcated by the imaging light rays IL1 and IL2 shown in FIG. 8. Specifically, in FIG. 8, the light flux region of the returning light of the illumination light is a region surrounded by the imaging light rays IL1 and IL2 (in FIG. 8, a region lower in the y direction from the imaging light ray IL1 and upper in the y direction from the imaging light ray IL2).

As shown in FIG. 8, the imaging light ray IL1 is represented by a straight line connecting an upper edge of the hole in the perforated mirror 45 at the pupil center position and an upper edge of the aperture in the slit 22 at the fundus position, The coordinate position of the upper edge of the hole in the perforated mirror 45 is (0, Sd/2). The coordinate position of the lower edge of the aperture in the slit 22 is (Lf, Lf×tan(ω/2)+Fd/2). Therefore, the imaging light ray IL1 is represented as in Equation (2).

[Equation 2]

$$y = \frac{Lf \times \tan\left(\frac{\omega}{2}\right) + \frac{Fd}{2} - \frac{Sd}{2}}{Lf} \times x + \frac{Sd}{2} \quad (2)$$

As shown in FIG. 8, the imaging light ray IL2 is represented by a straight line connecting a lower edge of the hole in the perforated mirror 45 at the pupil center position and a lower edge of the aperture in the slit 22 at the fundus position, The coordinate position of the lower edge of the hole in the perforated mirror 45 is (0, −Sd/2). The coordinate position of the lower edge of the aperture in the slit 22 is (Lf, Lf×tan(ω/2)−Fd/2). Therefore, imaging light ray IL2 can be derived in the same way as the illumination light ray IL1.

As described above, in case that the overlap region between the light flux region of the illumination region and the light flux region of the returning light thereof is located on a side of the fundus Ef from the posterior surface of lens, the occurrence of the flare on the posterior surface of the lens can be suppressed. As shown in FIG. 8, the position closest to the subject's eye E (or objective lens 46) in this overlap region is an intersecting point of the illumination light ray SL1 and the imaging light ray ILL or an intersecting point of the illumination light ray SL2 and the imaging light ray IL2. In FIG. 8, the x-coordinate position of the intersecting point of the illumination light ray SL1 and the imaging light ray IL1 is equal to the x-coordinate position of the intersecting point of the illumination light ray SL2 and the imaging light ray IL2.

As described above, when the x-coordinate position of the intersecting point of the illumination light ray SL1 and the imaging light ray IL1 is on the side of the fundus Ef from the position of the posterior surface of the lens, the occurrence of the flare on the posterior surface of the lens can be completely suppressed. The x-coordinate position Xlens of the intersecting point described above can be represented as in Equation (3) from Equation (1) and Equation (2) in a form independent of the imaging angle of view ω.

[Equation 3]

$$Xlens = \frac{Lf \times (Id - Sd)}{(Id - Sd + 2 \times Fd)} \quad (3)$$

From Equation (3), when Xlens>Ll is satisfied, the occurrence of the flare on the posterior surface of the lens can be completely suppressed. That is, when the slit width Fd described above, the distance Id described above, and the size Sd of the hole satisfy Equation (4), the occurrence of the flare on the posterior surface of the lens can be completely suppressed.

[Equation 4]

$$(Id - Sd) > \frac{2 \times Ll}{(Lf - Ll)} \times Fd \quad (4)$$

It should be noted that in Equation (4), in consideration of the pupil diameter Φ that can be photographed, Id<Φ needs to be satisfied. Here, the pupil diameter is defined in the specifications of the ophthalmic apparatus 1.

In some embodiments, in Equation (4), the relationship between the slit width Fd described above, the distance Id described above, and the size Sd of the hole described above is determined using parameter(s) representing the structure of the eyeball. Examples of the parameter(s) representing the structure of the eyeball include the parameter(s) of the schematic eye. Examples of the schematic eye include the Gullstrand schematic eye, and the Navarro schematic eye ("Off-axis aberrations of a wide-angle schematic eye model" (I. Escudero-Sanz and R. Navarro, Optical Society of America, August 1999, Vol. 16, No. 8, pp. 1881-1891)). For example, when the anterior surface of the cornea position, the posterior surface of the lens position, and the fundus position with reference to the pupil center position are defined using the parameters in the Navarro schematic eye, respectively, the following values are defined: La=3.6 [mm], Ll=4 [mm], Lf=20 [mm].

When Ll and Lf derived from the Navarro schematic eye are used, Equation (4) can be represented as in Equation (5).

[Equation 5]

$$(Id - Sd) > \frac{1}{2} \times Fd \quad (5)$$

When the slit width Fd described above, the distance Id described above, and the size Sd of the hole described above are set so as to satisfy at least Equation (4) or Equation (5) in the optical system shown in FIG. 1, the ophthalmic apparatus that can completely suppress the occurrence of the flare on the posterior surface of the lens can be provided.

<Suppression of the Occurrence of the Flare on the Anterior Surface of the Cornea>

Next, in the coordinate system defined as shown in FIG. 7, the x-coordinate position of the position of an intersection point of the illumination light ray and the imaging light ray is obtained in order to specify the limit(s) of the overlap region between the light flux region of the illumination region and the light flux region of the imaging light that causes the flare on the anterior surface of cornea.

Figure 9:
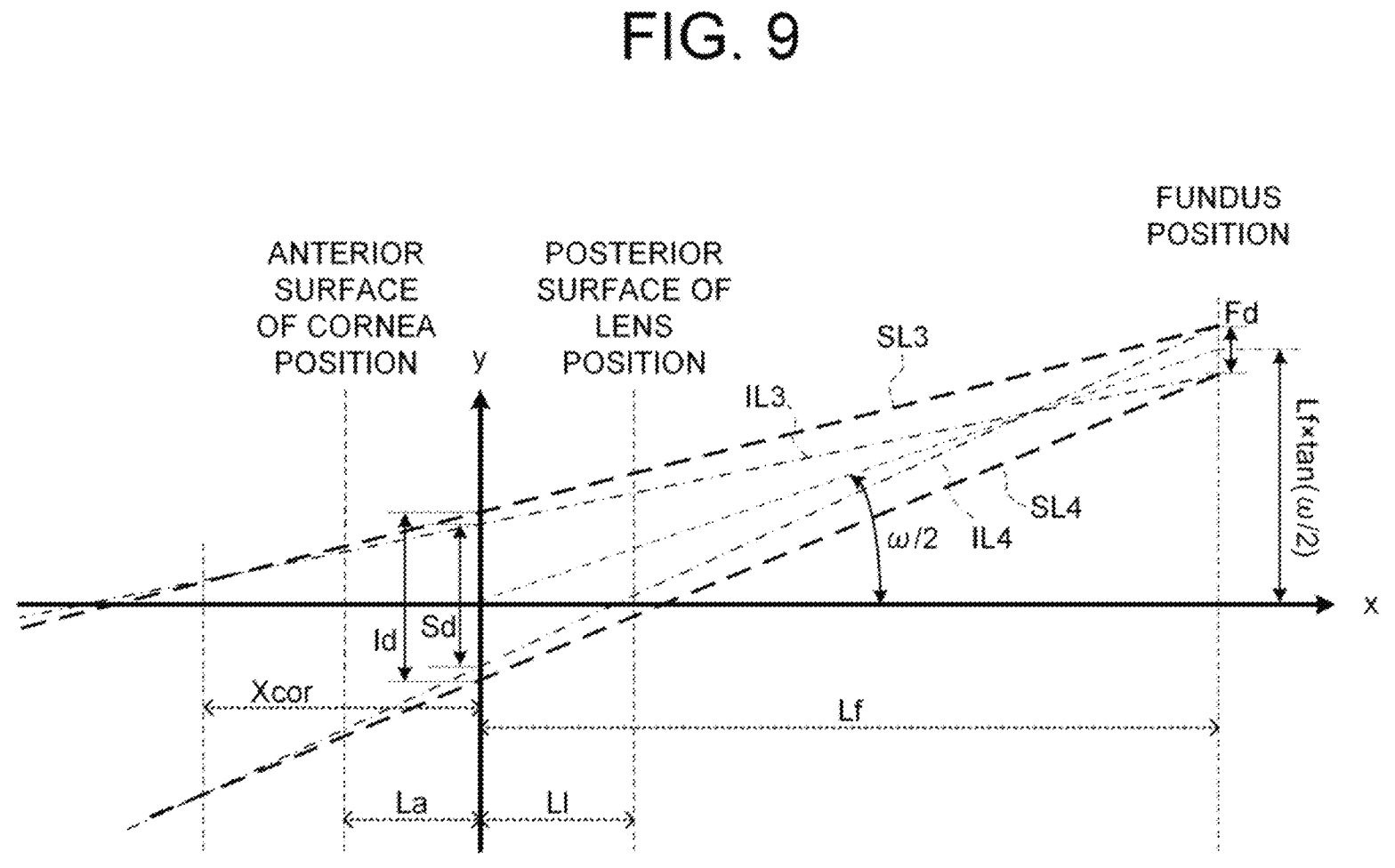

FIG. 9 shows a diagram explaining the overlap region between the light flux region of the illumination light and the light flux region of the imaging light that causes the flare on the anterior surface of cornea. In FIG. 9, parts similar to those in FIG. 8 are denoted by the same reference symbols, and description thereof is omitted as appropriate.

In this case, the light flux region of the illumination region is demarcated by the illumination light rays SL3 and SL4 shown in FIG. 9. Specifically, in FIG. 9, the light flux region of the illumination light passing through the aperture 21A of the iris aperture 21 is an upper region in the y direction from the illumination light ray SL3, and the light flux region of the illumination light passing through aperture 21B of the iris aperture 21 is a lower region in the y direction from illumination light ray SL4.

As shown in FIG. 9, the illumination light ray SL3 is represented by a straight line connecting a lower edge of the aperture 21A of the iris aperture 21 (the upper edge of the light shielding region including the optical axis position in the iris aperture 21) at the pupil center position and a lower edge of the aperture in the slit 22 at the fundus position. The coordinate position of the lower edge of the aperture 21A is (0, Id/2). The coordinate position of the upper edge of the aperture in the slit 22 is (Lf, Lf×tan(ω/2)+Fd/2). Therefore, the illumination light ray SL3 is represented as in Equation (6).

[Equation 6]

$$y = \frac{Lf \times \tan\left(\frac{\omega}{2}\right) + \frac{Fd}{2} - \frac{Id}{2}}{Lf} \times x + \frac{Id}{2} \quad (6)$$

As shown in FIG. 9, the illumination light ray SL4 is represented by a straight line connecting an upper edge of the aperture 21B of the iris aperture 21 (the lower edge of the light shielding region including the optical axis position in the iris aperture 21) at the pupil center position and a lower edge of the aperture in the slit 22 at the fundus position. The coordinate position of the lower edge of the aperture 21A is (0, −Id/2). The coordinate position of the lower edge of the aperture in the slit 22 is (Lf, Lf×tan(ω/2)−Fd/2). Therefore, illumination light ray SL4 can be derived in the same way as the illumination light ray SL3.

On the other hand, the light flux region of the returning light of the illumination region is demarcated by the imaging light rays IL3 and IL4 shown in FIG. 9. Specifically, in FIG. 9, the light flux region of the returning light of the illumination light is a region surrounded by the imaging light rays IL3 and IL4.

As shown in FIG. 9, the imaging light ray IL3 is represented by a straight line connecting an upper edge of the hole in the perforated mirror 45 at the pupil center position and a lower edge of the aperture in the slit 22 at the fundus position, The coordinate position of the upper edge of the hole in the perforated mirror 45 is (0, Sd/2). The coordinate position of the upper edge of the aperture in the slit 22 is (Lf, Lf×tan(ω/2)−Fd/2). Therefore, the imaging light ray IL3 is represented as in Equation (7).

[Equation 7]

$$y = \frac{Lf \times \tan\left(\frac{\omega}{2}\right) - \frac{Fd}{2} - \frac{Sd}{2}}{Lf} \times x + \frac{Sd}{2} \quad (7)$$

As shown in FIG. 9, the imaging light ray IL4 is represented by a straight line connecting a lower edge of the hole in the perforated mirror 45 at the pupil center position and an upper edge of the aperture in the slit 22 at the fundus position, The coordinate position of the lower edge of the hole in the perforated mirror 45 is (0, −Sd/2). The coordinate position of the upper edge of the aperture in the slit 22 is (Lf, Lf×tan(ω/2)+Fd/2). Therefore, imaging light ray IL4 can be derived in the same way as the illumination light ray IL3.

As described above, in case that the overlap region between the light flux region of the illumination region and the light flux region of the returning light thereof is located on a side of the fundus Ef from the anterior surface of cornea, the occurrence of the flare on the anterior surface of cornea can be suppressed. As shown in FIG. 9, the position closest to the to the fundus Ef in this overlap region is an intersecting point of the illumination light ray SL3 and the imaging light ray IL3, or an intersecting point of the illumination light ray SL4 and the imaging light ray IL4. In FIG. 9, the x-coordinate position of the intersecting point of the illumination light ray SL3 and the imaging light ray IL3 is equal to the x-coordinate position of the intersecting point of the illumination light ray SL4 and the imaging light ray IL4.

As described above, when the x-coordinate position of the intersecting point of the illumination light ray SL3 and the imaging light ray IL3 is on the side of the subject's eye E from the position of the anterior surface of cornea, the occurrence of the flare on the anterior surface of cornea can be completely suppressed. The x-coordinate position Xcor of the intersecting point described above can be represented as in Equation (8) from Equation (6) and Equation (7) in a form independent of the imaging angle of view ω.

[Equation 8]

$$Xcor = \frac{Lf \times (Id - Sd)}{(Id - Sd - 2 \times Fd)} \quad (8)$$

From Equation (8), when Xcor<−La is satisfied, the occurrence of the flare on anterior surface of cornea can be completely suppressed. That is, when the slit width Fd described above, the distance Id described above, and the size Sd of the hole satisfy Equation (9), the occurrence of the flare on the anterior surface of cornea can be completely suppressed.

[Equation 9]

$$\frac{2 \times La}{(Lf + La)} \times Fd < (Id - Sd) < 2 \times Fd \quad (9)$$

It should be noted that in Equation (9), in consideration of the pupil diameter Φ that can be photographed, Id<Φ needs to be satisfied. Here, the pupil diameter is defined in the specifications of the ophthalmic apparatus 1.

By the way, in the process of deriving Equation (9), it is used that (Id−Sd−2×Fd)<0 is satisfied. The reasons for this are as follows.

For example, assuming that (Id−Sd−2×Fd)>0, Equation (10) needs to be satisfied to satisfy Xlens>Ll on the side of the posterior surface of lens, as in Equation (4).

[Equation 10]

$$(Id - Sd) > \frac{2 \times Ll}{(Lf - Ll)} \times Fd \quad (10)$$

In addition, Equation (11) needs to be satisfied to satisfy Xcor<−La on the side of the anterior surface of cornea, as in Equation (9).

[Equation 11]

$$2 \times Fd < (Id - Sd) < \frac{2 \times La}{(Lf + La)} \times Fd \quad (11)$$

When the right-hand side of Equation (10) and the left-hand side of Equation (11) are compared and (2×Ll<Lf) is satisfied, Equation (12) is derived.

[Equation 12]

$$2 \times Fd < (Id - Sd) < \frac{2 \times La}{(Lf + La)} \times Fd \quad (12)$$

Here, from Equation (12), an inequality of 1<La/(Lf+La) is obtained, however this inequality cannot exist.

When the right-hand side of Equation (10) and the left-hand side of Equation (11) are compared, an inequality of (2×Ll>Lf) is derived. However, this inequality cannot exist either due to the structure of the eye.

From the above, in the process of deriving Equation (9), (Id−Sd−2×Fd)<0 is satisfied.

In some embodiments, in Equation (9), the relationship between the slit width Fd described above, the distance Id described above, and the size Sd of the hole described above is determined using parameter(s) representing the structure of the eyeball. Examples of the parameter(s) representing the structure of the eyeball include the parameter(s) of the schematic eye. Examples of the schematic eye include the Gullstrand schematic eye, and the Navarro schematic eye.

Using Ll and Lf derived from the Navarro schematic eye as described above, Equation (9) can be represented as in Equation (13).

[Equation 13]

$$\frac{18}{59} \times Fd < (Id - Sd) < 2 \times Fd \quad (13)$$

When the slit width Fd described above, the distance Id described above, and the size Sd of the hole described above are set so as to satisfy at least Equation (9) or Equation (13) in the optical system shown in FIG. 1, the ophthalmic apparatus that can completely suppress the occurrence of the flare on the anterior surface of cornea can be provided.

In some embodiments, in order to completely suppress both the occurrence of the flare on the posterior surface of lens and the occurrence of the flare on the anterior surface of cornea, the slit width Fd described above, the distance Id described above, and the size Sd of the hole described above are set.

In this case, in order to satisfy both Equation (4) and Equation (9), the slit width Fd described above, the distance Id described above, and the size Sd of the hole described above are set.

Specifically, when $(La-Ll)\times Lf < (2\times Ll-Lf)$ is satisfied, the slit width Fd described above, the distance Id described above, and the size Sd of the hole described above are set so as to satisfy Equation (14).

[Equation 14]

$$\frac{2 \times Ll}{(Lf - Ll)} \times Fd < (Id - Sd) < 2 \times Fd \qquad (14)$$

It should be noted that in Equation (14), in consideration of the pupil diameter $\Phi$ that can be photographed, $Id < \Phi$ needs to be satisfied. Here, the pupil diameter is defined in the specifications of the ophthalmic apparatus 1.

For example, in case of using the Navarro schematic eye, Equation (14) can be represented as in Equation (15).

[Equation 15]

$$\frac{1}{2} \times Fd < (Id - Sd) < 2 \times Fd \qquad (15)$$

It should be noted that in Equation (15), in consideration of the pupil diameter $\Phi$ that can be photographed, $Id < \Phi$ needs to be satisfied. Here, the pupil diameter is defined in the specifications of the ophthalmic apparatus 1.

On the other hand, when $(La-Ll)\times Lf > (2\times Ll-Lf)$ is satisfied, the slit width Fd described above, the distance Id described above, and the size Sd of the hole described above are set so as to satisfy Equation (16).

[Equation 16]

$$\frac{2 \times La}{(Lf + La)} \times Fd < (Id - Sd) < 2 \times Fd \qquad (16)$$

For example, in case of using the Navarro schematic eye, Equation (16) can be represented as in Equation (17).

[Equation 17]

$$\frac{18}{59} \times Fd < (Id - Sd) < 2 \times Fd \qquad (17)$$

When the slit width Fd described above, the distance Id described above, and the size Sd of the hole described above are set so as to satisfy at least Equation (16) or Equation (17) in the optical system shown in FIG. 1, the ophthalmic apparatus that can completely suppress the occurrence of the flare on the posterior surface of lens and the occurrence of the flare on the anterior surface of cornea can be provided.

The perforated mirror 45 is an example of the "imaging aperture" according to the embodiments.

MODIFICATION EXAMPLES

First Modification Example to Fourth Modification Example

In the embodiments described above, for example, the slit width Fd described above, the distance Id described above, and the size Sd of the hole described above are set in the inspection process or the shipping process of the ophthalmic apparatus 1. However, the configuration according to the embodiments is not limited to this. In the first modification example to the fourth modification example of the embodiments, the slit width Fd described above, the distance Id described above, and the size Sd of the hole described above are set in accordance with the ocular structure of the subject's eye E.

Hereinafter, the first modification example to the fourth modification example of the embodiments will be described focusing on the differences from the embodiments.

[Configuration of Optical System]

The difference between configurations of optical systems of the ophthalmic apparatuses according to the first modification example to the fourth modification example of the embodiments and the configuration of the optical system of the ophthalmic apparatus 1 according to the embodiments is the iris aperture 21, the slit 22, and the perforated mirror 45.

The iris aperture 21 according to the first modification example and the second modification example of the embodiments is configured to change the size of the opening shape of the apertures 21A and 21B. By changing the size of the opening shape of the apertures 21A and 21B, the distance between the apertures 21A and 21B is changed.

Figure 10A:
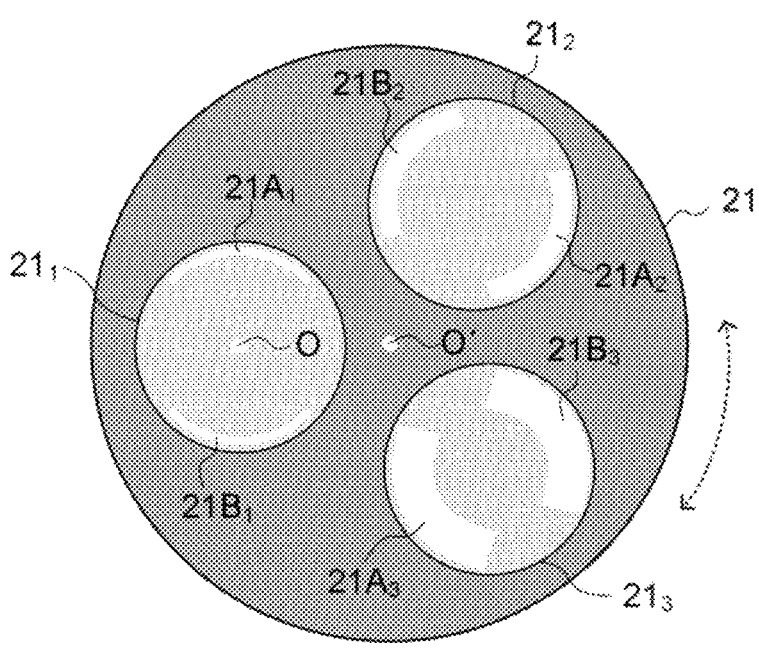
FIG. 10A is a schematic diagram illustrating an example of a configuration of an optical system of an ophthalmic apparatus according to a first modification example of the embodiments.
Figure 10B:
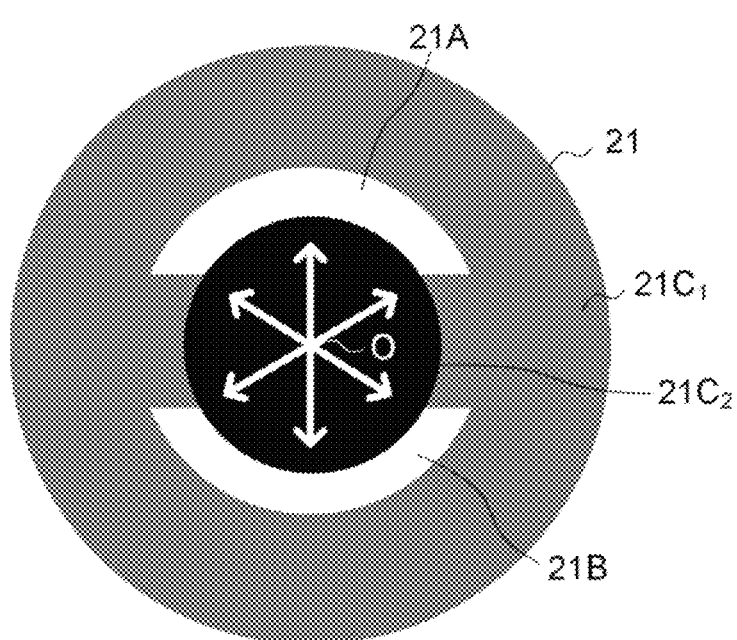
FIG. 10B is a schematic diagram illustrating an example of a configuration of an optical system of an ophthalmic apparatus according to a second modification example of the embodiments.

FIG. 10A and FIG. 10B show examples of a configuration of the iris aperture 21 according to the first modification example and the second modification example of the embodiments. FIG. 10A represents an example of a configuration of the iris aperture 21 according to the first modification example of the embodiments. FIG. 10B represents an example of a configuration 21 of the iris aperture 21 according to the second modification example of the embodiments. FIG. 10A and FIG. 10B schematically represent examples of the configuration of the iris aperture 21 in FIG. 1 when viewed from a direction of the optical axis O.

For example, as shown in FIG. 10A, the iris aperture 21 according to the first modification example includes a turret provided orthogonally to the rotation axis O' which is parallel to the optical axis O. The turret is provided so as to be capable of rotating around the rotation axis O'. The turret is provided with a plurality of iris apertures on a circumference centered on the rotation axis O'. By rotating the turret around the rotation axis O', the plurality of iris apertures (iris apertures $21_1$ to $21_3$ in FIG. 10A) can be selectively placed on the optical axis O. The turret can be rotated automatically or manually. For example, a driving mechanism (21D), which receives control from the controller 100, can rotate the turret around the rotation axis O'. In FIG. 10A, the size of the opening shape increases in the order of the iris aperture $21_1$, the iris aperture $21_2$, and the iris aperture $21_3$. In the iris aperture $21_1$, apertures $21A_1$ and $21B_1$ are formed. In the iris aperture $21_2$, apertures $21A_2$ and $21B_2$ are formed. In the iris aperture $21_3$, apertures $21A_3$ and $21B_3$ are formed.

Alternatively, as shown in FIG. 10B, for example, the iris aperture 21 according to the second modification example includes an optical member $21C_1$ provided substantially orthogonally to the optical axis O and an disk-shaped shielding plate $21C_2$ provided substantially orthogonally to the optical axis O. In the optical member $21C_1$, the apertures 21A and 21B are formed. A length of a radius of the shielding plate $21C_2$ can be changed. A part of the circumference of the shielding plate $21C_2$ constitutes inner diameters of the apertures 21A and 21B. A mechanism not shown in the figure can change the length of the radius of the shielding plate $21C_2$. The length of the radius of the shielding plate $21C_2$ can be automatically or manually changed. For example, the mechanism which receives control from the controller 100 can change the length of the radius of the shielding plate $21C_2$. By changing the size of the inner diameters of the apertures 21A and 21B in this way, the size of the opening shape of the apertures 21A and 21B of the iris aperture 21 can be changed.

It should be noted that a case in which the size of the inner diameters of the apertures 21A and 21B are configured to be changed is described in FIG. 10B. However, the size of the outer diameters of the apertures 21A and 21B may be configured to be changed. In this case, by changing the size of the outer diameters of the apertures 21A and 21B, the size of the opening shape of the apertures 21A and 21B of the iris aperture 21 can be changed.

Thus, by reducing the size of the opening shape of at least one of the apertures 21A and 21B, the light amount of the illumination light passing through the iris aperture 21 can be reduced. By increasing the size of the opening shape of at least one of the apertures 21A and 21B, the light amount of the illumination light passing through the iris aperture 21 can be increased.

Further, the slit 22 according to the third modification example and the fourth modification example of the embodiments is configured to change the size of the opening shape of the aperture.

Figure 11A:
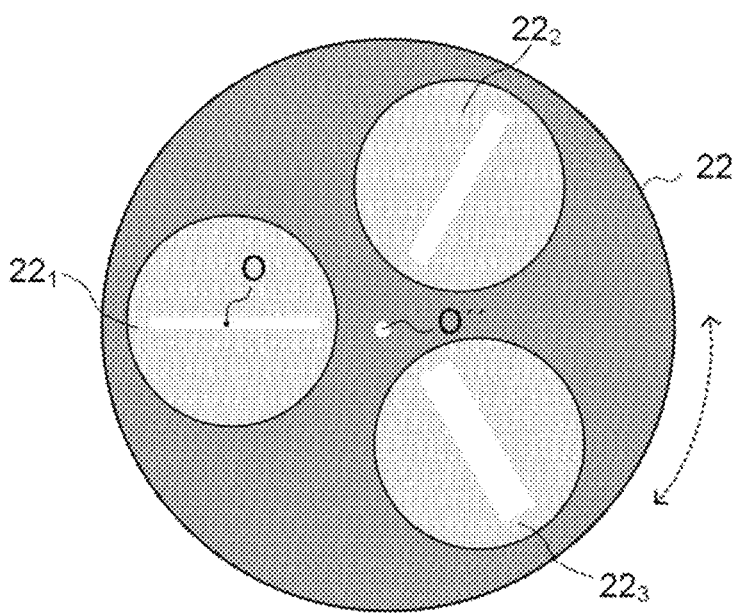
FIG. 11A is a schematic diagram illustrating an example of a configuration of an optical system of an ophthalmic apparatus according to a third modification example of the embodiments.
Figure 11B:
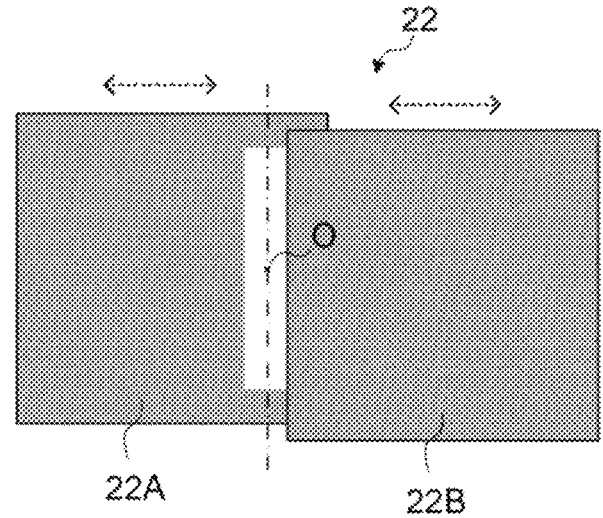
FIG. 11B is a schematic diagram illustrating an example of a configuration of an optical system of an ophthalmic apparatus according to a fourth modification example of the embodiments.

FIG. 11A and FIG. 11B show examples of a configuration of the slit 22 according to the third modification example and the fourth modification example of the embodiments. FIG. 11A represents an example of a configuration of the slit 22 according to the third modification example of the embodiments. FIG. 11B represents an example of a configuration of the slit 22 according to the fourth modification example of the embodiments. FIG. 11A and FIG. 11B schematically represent examples of the configuration of an slit 22 in FIG. 1 when viewed from a direction of an optical axis O.

For example, as shown in FIG. 11A, the slit 22 according to the third modification example includes a turret provided orthogonally to the rotation axis O" which is parallel to the optical axis O. The turret is provided so as to be capable of rotating around the rotation axis O". The turret is provided with a plurality of slits on a circumference centered on the rotation axis O". By rotating the turret around the rotation axis O", a plurality of slits (slits $22_1$ to $22_3$ in FIG. 11A) can be selectively placed on the optical axis O. The turret can be rotated automatically or manually. For example, the driving mechanism (22D), which receives control from the controller 100, can rotate the turret around the rotation axis O". In FIG. 11A, the size of the opening shape increases in the order of the slit $22_1$, the slit $22_2$, and the slit $22_3$.

Alternatively, as shown in FIG. 11B, for example, the slit 22 according to the fourth modification example includes shielding plates 22A and 22B. The shielding plates 22A and 22B can be slid in a direction substantially orthogonal to the optical axis O. The shielding plates 22A and 22B are slid in opposite directions each other so that the slit width is changed lineally symmetrically with respect to a slit center line passing through the optical axis O. The shielding plates 22A and 22B are slid automatically or manually. For example, the driving mechanism (22D) slides the shielding plates 22A and 22B. For example, the driving mechanism (22D), which receives control from the controller 100 described below, slides the shielding plates 22A and 22B.

Thus, by reducing the width (size of the opening shape) of slit 22, the light mount of the illumination light passing through slit 22 can be reduced. By increasing the width of slit 22, the light amount of the illumination light passing through slit 22 can be increased.

Further, a size of the opening shape of the hole (aperture) in the perforated mirror 45 according to the embodiments or the first modification example to the fourth modification example described above can be changed using a known mechanism. In some embodiments, the movement mechanism changes the size of the opening shape of the hole in the perforated mirror 45 under the control from the controller 100. In some embodiments, the perforated mirror 45 includes a reflective member with a hole in the central region, and an aperture member disposed inside or near the hole in the reflective member. A mechanism drives the aperture member to change the size of the opening shape of the hole, under control from the controller 100.

Thus, by reducing the size of the opening shape of the perforated mirror 45, the light amount of the returning light of the illumination light passing through the hole can be reduced. By increasing the size of the opening shape of the perforated mirror 45, the light amount of the returning light of the illumination light passing through the hole can be increased.

[Configuration of Control System]

Figure 12:
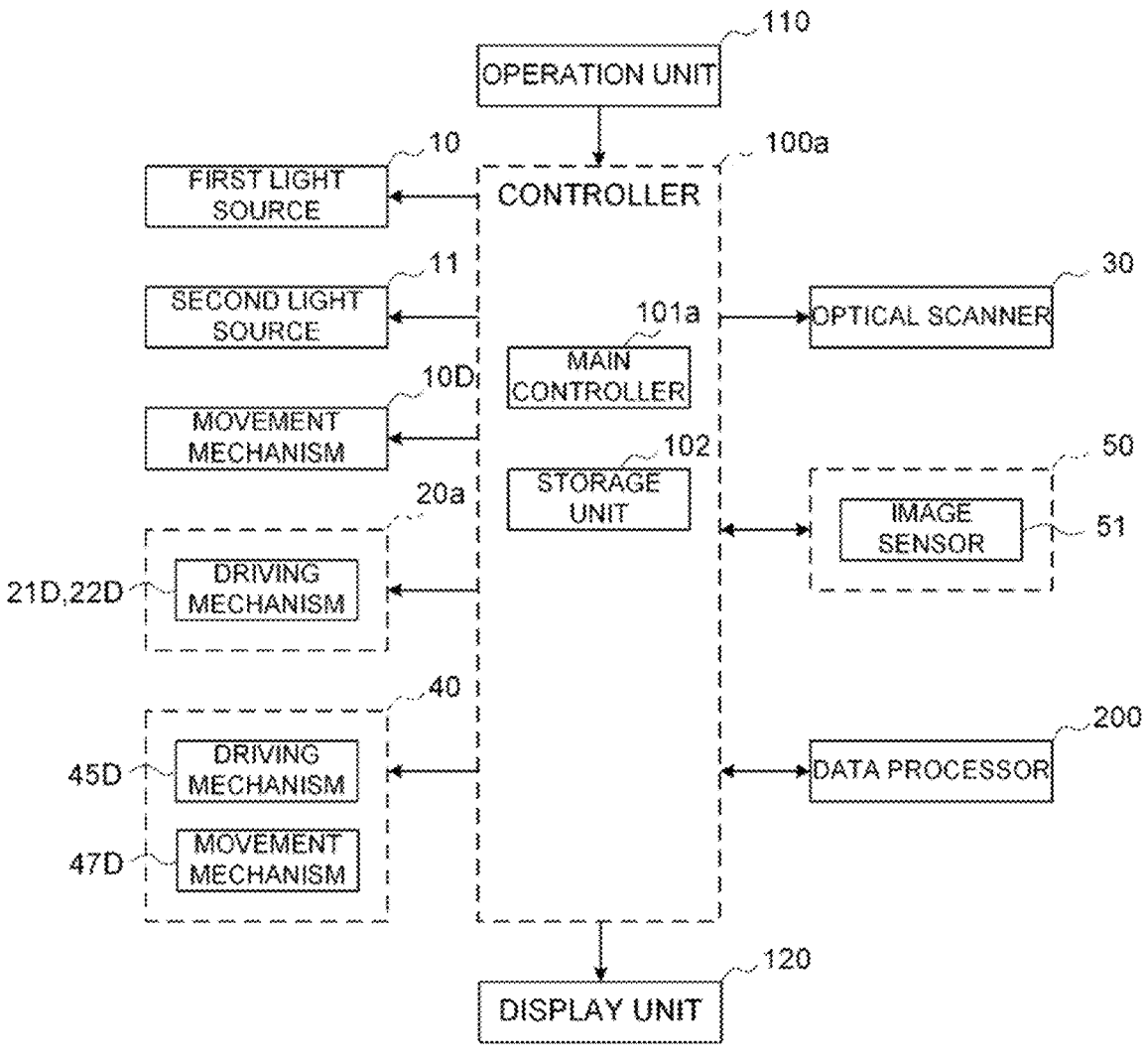
FIG. 12 is a schematic diagram illustrating an example of a configuration of a control system of the ophthalmic apparatus according to the first modification example to the fourth modification example of the embodiments.

FIG. 12 shows a block diagram of an example of the configuration the control system (processing system) of the ophthalmic apparatus according to the first modification example to the fourth modification example of the embodiments. In FIG. 12, parts similar to those in FIG. 2 are denoted by the same reference symbols, and description thereof is omitted as appropriate.

The difference between configurations of control systems of the ophthalmic apparatuses according to the first modification example to the fourth modification example of the embodiments and the configuration of the control system of the ophthalmic apparatus 1 according to the embodiments is the iris aperture 21, the slit 22, and the perforated mirror 45.

The driving mechanism 21D, for example, rotates the turret shown in FIG. 10A, or changes the radius of the shielding plate $21C_2$ shown in FIG. 10B. The driving mechanism 21D, which receives control from the controller 100, can rotate the turret shown in FIG. 10A, or change the radius of the shielding plate $21C_2$ shown in FIG. 10B.

In addition to the functions of the driving mechanism 22D in the embodiments, for example, the driving mechanism 22D can also rotate the turret shown in FIG. 11A or slide shielding plates 22A and 22B shown in FIG. 11B. The driving mechanism 22D, which receives control from the controller 100, can rotate the turret shown in FIG. 11A or slide the shielding plates 22A and 22B shown in FIG. 11B.

The driving mechanism 45D changes the size of the opening shape of the hole, by driving the aperture member disposed inside or near the hole in the reflective member included in the perforated mirror 45. The driving mechanism 45D can driver the aperture member under the control from the controller 100.

The main controller 101 controls at least one of the driving mechanisms 21D, 22D, and 45D, in accordance with the ocular structure of the subject's eye E.

Examples of the ocular structure of the subject's eye E include the distance La in the optical axis direction of the optical system between the anterior surface of cornea position and the pupil center position of the subject's eye E, the distance Ll in the optical axis direction of the optical system between the pupil center position and the posterior surface of lens position, and the distance Lf in the optical axis direction of the optical axis between the pupil center position and the fundus position. At least one of the distances La, Ll, and Lf can be acquired from a measured value obtained by a known optical coherence tomography apparatus. The main controller 101 can acquire at least one of the distances La, Ll, and Lf from an optical coherence tomography apparatus provided outside of the ophthalmic apparatus 1. In some embodiments, the main controller 101 acquires a part of the distances La, Ll, and Lf from the optical coherence tomography apparatus, acquires the rest from the parameter(s) of the schematic eye, and controls at least one of the driving mechanisms 21D, 22D, and 45D based on the acquired parameters representing the structure of the eyeball.

The main controller 101 controls at least one of the driving mechanisms 21D, 22D, and 45D so as to satisfy Equation (4), Equation (5), Equation (9), Equation (13), Equation (14), Equation (15), Equation (16), or Equation (17), in accordance with the ocular structure of the subject's eye E as described above.

For example, control information is stored in memory 102. In the control information, a control content for setting at least one of the distance of the apertures 21A and 21B of the iris aperture 21, the slit width of the slit 22, and the size of the opening shape of the hole of the perforated mirror 45 is associated in advance for each of one or more parameters indicating the ocular structure of the subject's eye. The main controller 101 can control at least one of the iris aperture 21, the slit 22, and the perforated mirror 45 in accordance with the ocular structure of the subject's eye E, by referring to the control information stored in the storage unit 102.

According to the modification examples of the embodiments, the distance between the apertures 21A and 21B of the iris aperture 21, the slit width of the slit 22, and the size of the opening shape of the hole of the perforated mirror 45 are changed. Thereby, the occurrence of the flare can be completely suppressed, regardless of the ocular structure of the subject's eye.

Fifth Modification Example

The configuration of the ophthalmic apparatus according to the embodiments or the modification examples thereof is not limited to the configurations explained in the embodiments or the modification examples thereof described above. In the fifth modification example of the embodiments, the optical system is configured according to Badal's principle. This allows to keep the size of the slit image at the fundus Ef constant, regardless the dioptric power of the subject's eye E.

Hereinafter, the configuration of the ophthalmic apparatus according to the fifth modification example of the embodiments will be described mainly about the differences from the embodiments.

FIG. 13 shows an example of the configuration of the ophthalmic apparatus according to the fifth modification example of the embodiments. In FIG. 13, parts similar to those in FIG. 1 are denoted by the same reference symbols, and description thereof is omitted as appropriate.

The configuration of an ophthalmic apparatus 1a according to the fifth modification example of the embodiments is mainly different from that of the ophthalmic apparatus 1 according to the embodiments shown in FIG. 1 in that an illumination optical system 20a is provided instead of the illumination optical system 20.

The configuration of illumination optical system 20a differs from the configuration of the illumination optical system 20 in that a relay lens system RL1 is provided instead of the relay lens 23. That is, the relay lens system RL1 is arranged between the optical scanner 30 and the slit 22, in the same way as the relay lens 23. The relay lens system RL1, relay lenses 41 and 44, and the objective lens 46 constitute a Badal optical system.

FIG. 14 shows an example of a configuration of the relay lens system RL1 according to the fifth modification example of the embodiments. In FIG. 14, the relay lens system RL1 and the optical scanner 30 are illustrated for convenience of explanation. Further, in FIG. 14, the relay lens system RL1 is assumed to include three lenses.

In the same way as the relay lens 23, the relay lens system RL1 includes one or more lenses. A back focal position F1 of the relay lens system RL1 is arranged at a position substantially conjugate optically to the iris of the subject's eye E.

That is, the optical scanner 30, which is arranged at a position substantially conjugate optically to the iris of the subject's eye E as described above, is arranged at the back focal position F1 of the relay lens system RL1 or the vicinity of the back focal position F1. Therefore, even when the slit 22 is moved in the optical axis direction in accordance with the dioptric power of the subject's eye E, the size of the slit image (image formed by the light passing through the aperture formed in the slit 22) projected onto the fundus Ef does not change. This means that the projection magnification of the slit image onto the fundus Ef does not change even when the slit 22 moves in the optical axis direction.

The operation of the ophthalmic apparatus 1a according to the fifth modification example is similar to the operation of the ophthalmic apparatus 1 according to the embodiments. Thus, the detailed description of the operation will be omitted.

The relay lens system RL1 is an example of the "first relay lens system" according to the embodiments.

According to the fifth modification example, by arranging the optical scanner 30 at the back focal position F1 of the relay lens system RL1 (or the vicinity of the back focal position F1), the Badal optical system is configured with the relay lens system RL1, the relay lenses 41 and 42, and the objective lens 46.

This allows to keep the projected angle of view (projection magnification) of the slit image with reference to the visual axis of the subject's eye E (longitudinal and shorter directions of the slit 22) constant, regardless the dioptric power of the subject's eye E. As a result, the size of the slit image does not change regardless of the dioptric power of the subject's eye E. This allows to keep the deflection operation speed of the optical scanner 30 constant, and to simplify the control of the optical scanner 30.

In addition, since the projected angle of view (projection magnification) of the slit image with reference to the visual axis of the subject's eye E is constant regardless of the dioptric power of the subject's eye E, the illumination intensity of the slit image at the fundus Ef can be kept constant regardless of the dioptric power of the subject's eye E.

Further, in case of acquiring images at a predetermined imaging angle of view in the ophthalmic apparatus, since the projection magnification is constant as described above, this eliminates the need for a margin of the length in the longitudinal length of the slit 22 provided to acquire a slit image of a predetermined size.

Sixth Modification Example

The configuration of the ophthalmic apparatus according to the embodiments is not limited to the configuration of the ophthalmic apparatus described above. In the ophthalmic apparatus according to the sixth modification example of the embodiments, a relay lens system is positioned between the slit 22 and the iris aperture 21 to increase the degree of freedom in optical design.

Hereinafter, the configuration of the ophthalmic apparatus according to the sixth modification example of the embodiments will be described mainly about the differences from the fifth modification example of the embodiments.

FIG. 15 shows an example of the configuration of the ophthalmic apparatus according to the sixth modification example of the embodiments. In FIG. 15, parts similar to those in FIG. 13 are denoted by the same reference symbols, and description thereof is omitted as appropriate.

The configuration of the ophthalmic apparatus 1b according to the sixth modification example of the embodiments differs from that of the ophthalmic apparatus 1a according to the fourth modification example of the embodiments in that an illumination optical system 20b is provided instead of the illumination optical system 20a.

The configuration of illumination optical system 20b differs from the configuration of the illumination optical system 20a in that a relay lens system RL2 is provided. That is, the relay lens system RL2 is arranged between the slit 22 and the iris aperture 21.

FIG. 16 shows an example of a configuration of the relay lens system RL2 according to the sixth modification example of the embodiments. In FIG. 16, the iris aperture 21, the relay lens system RL2, the slit 22, the relay lens system RL1, and the optical scanner 30 are illustrated for convenience of explanation. Further, in FIG. 16, the relay lens system RL2 is assumed to include two lenses.

In the same way as the relay lens system RL1, the relay lens system RL2 includes one or more lenses. The iris aperture 21 is arranged at a front focal position F2 of the relay lens system RL2 or the vicinity of the front focal position F2.

As described above, the iris aperture 21 is arranged at the front focal position F2 of the relay lens system RL2 or the vicinity of the front focal position F2. That is, the back focal position F1 of the relay lens system RL1 is the position substantially conjugate optically to the iris aperture 21, and the iris aperture 21 is arranged at the front focal position F2 of the relay lens system RL2. Therefore, the projection magnification from the iris aperture 21 to the optical scanner 30 (arranged at the back focal position F1) is determined by a focal distance f1 of the relay lens system RL1 and a focal distance f2 of the relay lens system RL2. In this case, the projection magnification is (f1/f2).

The ophthalmic apparatus is required to form images of the iris aperture 21 with a predetermined size on the iris of the subject's eye E. When the projection magnification from the iris of the subject's eye E to the optical scanner 30 via the objective lens 46 is a known projection magnification, an image of the iris aperture 21 of a predetermined size should be projected on the optical scanner 30. In this case, the projection magnification from the iris aperture 21 to the optical scanner 30 is determined by the focal distance f1 of the relay lens system RL1 and the focal distance f2 of the relay lens system RL2. Therefore, by changing at least one of the focal distances f1 and f2, the image of the iris aperture 60 can be easily formed on the iris of the subject's eye E with a predetermined size. In some embodiments, while the focal distance f1 remains fixed, the focal distance f2 is changed alone.

The focal distance f1 is a composite focal distance of the relay lens system RL1. In some embodiments, the relay lens system RL1 includes a plurality of the lenses with different dioptric powers, and changes the focal distance f1 by changing at least one of the lenses constituting the relay lens system RL1. In some embodiments, at least one of the lenses constituting the relay lens system RL1 is a lens whose dioptric power can be changed. Examples of the lens whose dioptric power can be changed include a liquid crystal lens, a liquid lens, and an Alvarez lens. Even when the focal distance f1 is changed, the back focal position of the relay lens system RL1 is arranged at a position substantially conjugate optically to the iris (pupil conjugate position) of the subject's eye E.

The focal distance f2 is a composite focal distance of the relay lens system RL2. In some embodiments, the relay lens system RL2 includes a plurality of the lenses with different dioptric powers, and changes the focal distance f2 by changing at least one of the lenses constituting the relay lens system RL2. In some embodiments, at least one of the lenses constituting the relay lens system RL2 is a lens whose dioptric power can be changed. Even when the focal distance f2 is changed, the front focal position of the relay lens system RL2 is arranged at a position substantially conjugate optically to the iris (pupil conjugate position) of the subject's eye E.

In addition, for imaging the fundus Ef, it is desirable to use a light source that emits a high-intensity light. However, light sources available for general use (light sources that are mass-produced) are limited in the size of the emitting surface (luminous area, output luminous flux cross section size). Thereby, the image of the iris aperture 21 should be projected onto the optical scanner 30 with a projection magnification corresponding to the size of the emitting surface of the light source.

According to the sixth modification example, by changing at least one of the focal distances f1 and f2, the projecting magnification from the iris aperture 21 to the optical scanner 30 can be changed. Thereby, the image of the iris aperture 21 with any size can be projected onto the optical scanner 30 with the desired size. This allows to project the image of the iris aperture 21 with a desired size onto the optical scanner 30 by simply changing at least one of the focal distances f1 and f2 even when the size of the emitting surface of the light source is different and to improve the degree of freedom in designing optical systems. In particular, this allows to fix the movement amount of the slit 22 in response to changes in the dioptric power of the subject's eye E (sensitivity of the movement of the slit 22 in response to changes in the dioptric power) by fixing the focal distance f1 and changing the focal distance f2 alone, and to further improve the degree of freedom in designing optical systems.

The operation of the ophthalmic apparatus 1b according to the sixth modification example is similar to the operation of the ophthalmic apparatus 1a according to the fifth modification example. Thus, the detailed description of the operation will be omitted.

The relay lens system RL2 is an example of the "second relay lens system" according to the embodiments.

According to the sixth modification example, the effective diameter of one or more lenses constituting the relay lens system RL1 can be reduced.

The reason for this is that the slit 22, which is arranged at a position substantially conjugate optically to the fundus Ef of the subject's eye E, is arranged between the optical scanner 30 and the iris aperture 21. The slit 22 can be moved in the optical axis direction in accordance with the dioptric power of the subject's eye E. Here, the projection magnification from the iris aperture 21 to the optical scanner 30 is determined by the first distance, which is a distance between the optical scanner 30 and the relay lens system RL1, and the second distance, which is a distance between the iris aperture 60 and the relay lens system RL1. Thereby, when the first distance is shortened, the second distance should also be shortened. However, since it is necessary to maintain the conjugate relationship with the iris and the conjugate relationship with the fundus Ef while securing the space for movement of the slit 22 in the optical axis direction, the first distance becomes longer and the effective diameter of the relay lens system RL1 becomes larger. According to the sixth modification example, by providing the relay lens system RL2, the projection magnification can be adjusted using the relay lens system RL2 even if the first distance is shortened. This allows to shorten the first distance while maintaining the conjugate relationship with the iris and the conjugate relationship with the fundus Ef and securing the space for movement of the slit 22 in the optical axis direction, and to reduce the effective diameter of the one or more lenses constituting the relay lens system RL1.

Further, since the effective diameter of the one or more lenses constituting the relay lens system RL1 can be reduced, the length of the optical system from the optical scanner 30 to the light source 10 can be reduced.

Seventh Modification Example

It should be noted that in the sixth modification example, at least one of the focal distance f1 and the focal distance f2 may be changeable in accordance with the type of light source 10. The ophthalmic apparatus according to the seventh modification example of the embodiments can change at least one of the focal distance f1 and the focal distance f2 in accordance with the size of the emitting surface (luminous area, output luminous flux cross section size) of the light source 10.

For example, the relay lens system RL1 changes the focal distance f1 in accordance with the size of the emitting surface of the light source 10, in the same way as in the sixth modification example. For example, the relay lens system RL2 changes the focal distance f2 in accordance with the size of the emitting surface of the light source 10, in the same way as in the sixth modification example.

In some embodiments, the main controller 101 changes the focal distance f1 by controlling the relay lens system RL1 (or a lens whose dioptric power can be changed) in accordance with the size of the emitting surface of the light source 10 designated using the operation unit 110. In some embodiments, the main controller 101 changes the focal distance f2 by controlling the relay lens system RL2 (or a lens whose dioptric power can be changed) in accordance with the size of the emitting surface of the light source 10 designated using the operation unit 110.

[Actions and Effects]

Actions and effects of the ophthalmic apparatus according to the embodiments will be described.

An ophthalmic apparatus (1) according to some embodiments includes an illumination optical system (20), and an imaging optical system (40). The illumination optical system includes a slit (22) in which a slit-shaped aperture is formed and an iris aperture (21) in which two apertures (21A, 21B) are formed at positions away from an optical axis position, the iris aperture being arranged at a position substantially conjugate optically to an iris of a subject's eye (E) between a light source (10) and the slit, and is configured to generate slit-shaped illumination light using light from the light source and to guide the illumination light to a fundus (Ef) of the subject's eye. The imaging optical system includes an imaging aperture (perforated mirror 45) in which an aperture (hole) is formed, and configured to guide returning light of the illumination light to an image sensor (51), the returning light being guided from the fundus by pupil division and passing through the aperture formed in the imaging aperture. A width (Fd) of the slit-shaped aperture, a distance (Id) between the two apertures, and a size (Sd) of the aperture in the imaging aperture are set so that an overlap region of a light flux region of the illumination light and a light flux region of the returning light is located on a side of the fundus from a posterior surface of lens of the subject's eye within the eye of the subject eye.

According to such a configuration, the width of the slit-shaped aperture formed in the slit, the distance between the two apertures formed in the iris aperture, and the size of the aperture in the imaging aperture are set so that the overlap region of the light flux region of the illumination light and the light flux region of the returning light thereof is located on the side of the fundus from the posterior surface of lens of the subject's eye. Thereby, the occurrence of the flare on the posterior surface of lens can be completely suppressed. This allows to acquire high quality images of the subject's eye with a simple configuration.

In some embodiments, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, a distance between a pupil center of the subject's eye and the posterior surface of lens in an optical axis direction of the imaging optical system is represented as Ll, and a distance between the pupil center and the fundus in the optical axis direction is represented as Lf, the following equation is satisfied.

$$(Id-Sd)>(2{\times}Fd{\times}Ll/(Lf-Ll))$$

According to such a configuration, the width of the slit-shaped aperture formed in the slit, the distance between the two apertures formed in the iris aperture, and the size of the aperture in the imaging aperture can be set to satisfy simple mathematical expression(s). Thereby, the occurrence of the flare on the posterior surface of lens can be completely suppressed with ease.

In some embodiments, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, and a size of an image of the aperture in the imaging aperture on the iris is represented as Sd, the following equation is satisfied.

$$(Id-Sd)>(Fd/2)$$

According to such a configuration, the occurrence of the flare on the posterior surface of lens can be completely suppressed with ease using the parameter(s) of the Navarro schematic eye, when imaging the subject's eye having a standard structure of the eye.

In some embodiments, the width described above, the distance described above, and the size described above are further set so that the overlap region is located on a side of the subject's eye from the anterior surface of cornea of the subject's eye within the eye.

According to such a configuration, the width of the slit-shaped aperture formed in the slit, the distance between the two apertures formed in the iris aperture, and the size of the aperture in the imaging aperture are set so that the overlap region of the light flux region of the illumination light and the light flux region of the returning light thereof is located on the side of the subject's eye from the anterior surface of cornea of the subject's eye. Thereby, both the occurrence of the flare on the posterior surface of lens and the occurrence of the flare on the anterior surface of cornea can be completely suppressed. This allows to acquire higher quality images of the subject's eye with a simple configuration.

In some embodiments, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, a distance between a pupil center of the subject's eye and the posterior surface of lens in an optical axis direction of the imaging optical system is represented as Ll, a distance between the pupil center and the fundus in the optical axis direction is represented as Lf, a distance between an anterior surface of cornea of the subject's eye and the pupil center in the optical axis direction is represented as La, and the pupil center of the subject's eye is represented as an origin position, in case of $(La-Ll) \times Lf < (2 \times Ll-Lf) \times La$, the following equation is satisfied, $$(2 \times Fd \times Ll/(Lf-Ll)) < (Id-Sd) < (2 \times Fd)$$

and in case of $(La-Ll) \times Lf > (2 \times Ll-Lf) \times La$, the following equation is satisfied.

$$(2 \times Fd \times La/(Lf+La)) < (Id-Sd) < (2 \times Fd)$$

According to such a configuration, the width of the slit-shaped aperture formed in the slit, the distance between the two apertures formed in the iris aperture, and the size of the aperture in the imaging aperture can be set so as to satisfy simple mathematical expression(s). Thereby, both the occurrence of the flare on both of the posterior surface of lens and the occurrence of the flare on the anterior surface of cornea can be completely suppressed with ease.

In some embodiments, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, and the pupil center of the subject's eye is represented as an origin position, the following equation is satisfied.

$$(Fd/2) < (Id-Sd) < (2 \times Fd)$$

According to such a configuration, both the occurrence of the flare on the posterior surface of lens and the occurrence of the flare on the anterior surface of cornea can be completely suppressed with ease using the parameter(s) of the Navarro schematic eye, when imaging the subject's eye having a standard structure of the eye.

An ophthalmic apparatus (1) according to some embodiments includes an illumination optical system (20), and an imaging optical system (40). The illumination optical system includes a slit (22) in which a slit-shaped aperture is formed and an iris aperture (21) in which two apertures (21A, 21B) are formed at positions away from an optical axis position, the iris aperture being arranged at a position substantially conjugate optically to an iris of a subject's eye (E) between a light source (10) and the slit, and is configured to generate slit-shaped illumination light using light from the light source and to guide the illumination light to a fundus (Ef) of the subject's eye. The imaging optical system includes an imaging aperture (perforated mirror 45) in which an aperture (hole) is formed, and configured to guide returning light of the illumination light to an image sensor (51), the returning light being guided from the fundus by pupil division and passing through the aperture formed in the imaging aperture. A width (Fd) of the slit-shaped aperture, a distance (Id) between the two apertures, and a size (Sd) of the aperture in the imaging aperture are set so that an overlap region of a light flux region of the illumination light and a light flux region of the returning light is located on a side of the subject's eye from an anterior surface of cornea of the subject's eye within the eye of the subject eye.

According to such a configuration, the width of the slit-shaped aperture formed in the slit, the distance between the two apertures formed in the iris aperture, and the size of the aperture in the imaging aperture are set so that the overlap region of the light flux region of the illumination light and the light flux region of the returning light thereof is located on the side of the subject's eye from the anterior surface of cornea of the subject's eye. Thereby, the occurrence of the flare on the anterior surface of cornea can be completely suppressed. This allows to acquire high quality images of the subject's eye with a simple configuration.

In some embodiments, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, a distance between the pupil center and the fundus in the optical axis direction is represented as Lf, a distance between an anterior surface of cornea of the subject's eye and the pupil center in the optical axis direction is represented as La, and the pupil center of the subject's eye is represented as an origin position, the following equation is satisfied.

$$(2 \times Fd \times La/(Lf+La)) < (Id-Sd) < (2 \times Fd)$$

According to such a configuration, the width of the slit-shaped aperture formed in the slit, the distance between the two apertures formed in the iris aperture, and the size of the aperture in the imaging aperture can be set to satisfy simple mathematical expression(s). Thereby, the occurrence of the flare on the anterior surface of cornea can be completely suppressed with ease.

In some embodiments, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, and the pupil center of the subject's eye is represented as an origin position, the following equation is satisfied.

$$(18 \times Fd/59) < (Id-Sd) < (2 \times Fd)$$

According to such a configuration, the occurrence of the flare on the anterior surface of cornea of lens can be completely suppressed with ease using the parameter(s) of the Navarro schematic eye, when imaging the subject's eye having a standard structure of the eye.

In some embodiments, a size of the slit-shaped aperture can be changed.

According to such a configuration, the ophthalmic apparatus capable of suppressing the occurrence of the flare on the posterior surface of lens or the anterior surface of cornea and of acquiring the high quality images of the subject's eye, by changing the size of the slit-shaped aperture formed in the slit in accordance with the ocular structure of the subject's eye, can be provided.

In some embodiments, the distance between the two apertures can be changed.

According to such a configuration, the ophthalmic apparatus capable of suppressing the occurrence of the flare on the posterior surface of lens or the anterior surface of cornea and of acquiring the high quality images of the subject's eye, by changing the distance between the two apertures formed in the iris aperture in accordance with the ocular structure of the subject's eye, can be provided.

In some embodiments, a size of the aperture formed in the imaging aperture can be changed.

According to such a configuration, the ophthalmic apparatus capable of suppressing the occurrence of the flare on the posterior surface of lens or the anterior surface of cornea and of acquiring the high quality images of the subject's eye, by changing the size of the aperture formed in imaging aperture in accordance with the ocular structure of the subject's eye, can be provided.

In some embodiments, the imaging aperture is a perforated mirror (45) configured to couple an optical path of the illumination optical system with an optical path of the imaging optical system, the imaging optical system being arranged in an optical axis direction passing through the aperture in the imaging aperture, and to guide the illumination light reflected on a peripheral region of the aperture in the imaging aperture to the fundus.

According to such a configuration, the function of the imaging aperture is implemented using the perforated mirror coupling the optical path of the illumination optical system with the optical path of the imaging optical system. Thereby, while irradiating the illumination light onto the fundus by pupil division, the configuration of the optical systems can be simplified and the high quality images of the subject's eye can be acquired.

In some embodiments, the image sensor is configured to capture light receiving result of the returning light of the illumination light, the light receiving result corresponding to an irradiated position of the illumination on the fundus.

According to such a configuration, the ophthalmic apparatus capable of suppressing the occurrence of the flare and of acquiring the high quality images of the subject's eye with a simple configuration, by capturing the light receiving result of the returning light of the illumination light using the rolling shutter method, can be provided.

In some embodiments, the image sensor is a CMOS image sensor.

According to such a configuration, the high quality images of the subject's eye can be acquired with a simple configuration at a low cost while suppressing the occurrence of the flare.

The above-described some embodiments or the modification examples thereof are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include an axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The intraocular pressure measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus described above is provided. Such a program can be stored in any non-transitory computer-readable recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the fundus from a posterior surface of lens of the subject's eye within the eye of the subject eye, the overlap region being a region in which the illumination light and the returning light intersect, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, a distance between a pupil center of the subject's eye and the posterior surface of lens in an optical axis direction of the imaging optical system is represented as LI, and a distance between the pupil center and the fundus in the optical axis direction is represented as Lf, the following equation is satisfied:

$$(Id-Sd)>(2 \times Fd \times Ll/(Lf-Ll)).$$

2. An ophthalmic apparatus, comprising:

an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the fundus from a posterior surface of lens of the subject's eye within the eye of the subject eye, the overlap region being a region in which the illumination light and the returning light intersect, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, and a size of an image of the aperture in the imaging aperture on the iris is represented as Sd, the following equation is satisfied:

$$(Id-Sd)>(Fd/2).$$

3. The ophthalmic apparatus of claim 1, wherein the width, the distance, and the size are further set so that the overlap region is located on a side of the subject's eye from the anterior surface of cornea of the subject's eye within the eye.

4. An ophthalmic apparatus, comprising:

an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the subject's eye from a posterior surface of lens of the subject's eye within the eye of the subject eye, the overlap region being a region in which the illumination light and the returning light intersect, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, a distance between a pupil center of the subject's eye and the posterior surface of lens in an optical axis direction of the imaging optical system is represented as LI, a distance between the pupil center and the fundus in the optical axis direction is represented as Lf, a distance between an anterior surface of cornea of the subject's eye and the pupil center in the optical axis direction is represented as La, and the pupil center of the subject's eye is represented as an origin position, in case of $(La-Ll) \times Lf < (2 \times Ll-Lf) \times La$, the following equation is satisfied:

$$(2 \times Fd \times Ll/(Lf-Ll)) < (Id-Sd) < (2 \times Fd),$$

and in case of $(La-Ll) \times Lf > (2 \times Ll-Lf) \times La$, the following equation is satisfied:

$$(2 \times Fd \times La/(Lf+La)) < (Id-Sd) < (2 \times Fd).$$

5. An ophthalmic apparatus, comprising:

an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the fundus from a posterior surface of lens of the subject's eye within the eye of the subject eye, the overlap region being a region in which the illumination light and the returning light intersect, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, and the pupil center of the subject's eye is represented as an origin position, the following equation is satisfied:

$$(Fd/2) < (Id-Sd) < (2 \times Fd).$$

6. An ophthalmic apparatus, comprising:

an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the subject's eye from an anterior surface of cornea of the subject's eye within the eye of the subject eye, the overlap region being a region in which the illumination light and the returning light intersect, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, a distance between the pupil center and the fundus in the optical axis direction is represented as Lf, a distance between an anterior surface of cornea of the subject's eye and the pupil center in the optical axis direction is represented as La, and the pupil center of the subject's eye is represented as an origin position, the following equation is satisfied:

$$(2 \times Fd \times La/(Lf+La)) < (Id-Sd) < (2 \times Fd).$$

7. An ophthalmic apparatus, comprising:

an illumination optical system including a slit in which a slit-shaped aperture is formed and an iris aperture in which two apertures are formed at positions away from an optical axis position, the iris aperture being arranged at a position substantially conjugate optically to an iris of a subject's eye between a light source and the slit, and configured to generate slit-shaped illumination light using light from the light source and to guide the illumination light to a fundus of the subject's eye; and an imaging optical system including an imaging aperture in which an aperture is formed, and configured to guide returning light of the illumination light to an image sensor, the returning light being guided from the fundus by pupil division and passing through the aperture formed in the imaging aperture, wherein a width of the slit-shaped aperture, a distance between the two apertures, and a size of the aperture in the imaging aperture are set so that an overlap region of a light flux region of the illumination light and a light flux region of the returning light is located on a side of the subject's eye from an anterior surface of cornea of the subject's eye within the eye of the subject eye, the overlap region being a region in which the illumination light and the returning light intersect, the slit-shaped aperture can be arranged at a position substantially conjugate optically to the fundus, the aperture in the imaging aperture can be arranged at a position substantially conjugate optically to the iris, and when a width of an image of the aperture in the slit on the fundus is represented as Fd, a distance between the two apertures in the iris aperture on the iris is represented as Id, a size of an image of the aperture in the imaging aperture on the iris is represented as Sd, and the pupil center of the subject's eye is represented as an origin position, the following equation is satisfied;

$$(18 \times Fd/59) < (Id-Sd) < (2 \times Fd).$$

8. The ophthalmic apparatus of claim 1, wherein a size of the slit-shaped aperture can be changed.

9. The ophthalmic apparatus of claim 6, wherein a size of the slit-shaped aperture can be changed.

10. The ophthalmic apparatus of claim 1, wherein the distance between the two apertures can be changed.

11. The ophthalmic apparatus of claim 6, wherein the distance between the two apertures can be changed.

12. The ophthalmic apparatus of claim 1, wherein a size of the aperture formed in the imaging aperture can be changed.

13. The ophthalmic apparatus of claim 6, wherein
a size of the aperture formed in the imaging aperture can
be changed.

14. The ophthalmic apparatus of claim 1, wherein
the imaging aperture is a perforated mirror configured to
couple an optical path of the illumination optical sys-
tem with an optical path of the imaging optical system,
the imaging optical system being arranged in an optical
axis direction passing through the aperture in the imag-
ing aperture, and to guide the illumination light
reflected on a peripheral region of the aperture in the
imaging aperture to the fundus.

15. The ophthalmic apparatus of claim 6, wherein
the imaging aperture is a perforated mirror configured to
couple an optical path of the illumination optical sys-
tem with an optical path of the imaging optical system,
the imaging optical system being arranged in an optical
axis direction passing through the aperture in the imaging aperture, and to guide the illumination light
reflected on a peripheral region of the aperture in the
imaging aperture to the fundus.

16. The ophthalmic apparatus of claim 1, wherein
the image sensor is configured to capture light receiving
result of the returning light of the illumination light, the
light receiving result corresponding to an irradiated
position of the illumination on the fundus.

17. The ophthalmic apparatus of claim 6, wherein
the image sensor is configured to capture light receiving
result of the returning light of the illumination light, the
light receiving result corresponding to an irradiated
position of the illumination on the fundus.

18. The ophthalmic apparatus of claim 1, wherein
the image sensor is a CMOS image sensor.

19. The ophthalmic apparatus of claim 6, wherein
the image sensor is a CMOS image sensor.

* * * * *